United States Patent
Seibel et al.

(10) Patent No.: US 6,921,816 B2
(45) Date of Patent: Jul. 26, 2005

(54) CHIMERICAL PEPTIDE-NUCLEIC ACID FRAGMENT, PROCESS FOR PRODUCING THE SAME AND ITS FOR APPROPRIATELY INTRODUCING NUCLEIC ACIDS INTO CELL ORGANELLES AND CELLS

(75) Inventors: Peter Seibel, Obare Hainbachstrasse 2, Biedeakopf-Wallau 35216 (DE); Andrea Seibel, Albertshofen (DE)

(73) Assignee: Peter Seibel, Wurzburg (DE)

(*) Notice: Subject to any disclaimer, the term of this patent is extended or adjusted under 35 U.S.C. 154(b) by 0 days.

(21) Appl. No.: 08/765,244

(22) PCT Filed: Jun. 11, 1995

(86) PCT No.: PCT/DE95/00775
§ 371 (c)(1),
(2), (4) Date: Oct. 30, 1997

(87) PCT Pub. No.: WO95/34665
PCT Pub. Date: Dec. 21, 1995

(65) Prior Publication Data
US 2001/0008771 A1 Jul. 19, 2001

(30) Foreign Application Priority Data
Jun. 16, 1994 (DE) .......................................... 44 21 079

(51) Int. Cl.[7] .......................... C07H 21/04; C12Q 1/68; C12P 19/34; C07K 5/00; C07K 14/00
(52) U.S. Cl. ......................... 536/24.5; 435/6; 435/91.1; 530/350; 530/300
(58) Field of Search .......................... 435/6, 91.1, 455, 435/440, 322; 536/24.5, 23.1; 530/350, 300

(56) References Cited
U.S. PATENT DOCUMENTS
5,569,754 A * 10/1996 Williams et al. ........... 536/23.5
5,807,746 A * 9/1998 Lin et al. ..................... 435/375

FOREIGN PATENT DOCUMENTS
WO 9114696 * 10/1991
WO WO 95/34295 6/1995

OTHER PUBLICATIONS

Horwich et al, 1987, Journal of Cell Biology v105 (1987) p 663–677.*
Vestweber et al. "DNA–protein conjugates can enter mitochondria via the protein import pathway" Nature, vol. 338, p. 170–172.*
Anderson et al., 1981, "Sequence and organization of the human mitochondrial genome", Nature 290:457–465.
Arar et al., 1993, "Synthesis of oligonucleotide–peptide conjugates containing a KDEL signal sequence", Tetrahedron Lett. 34:8087–8090.
Aslanidis et al., 1990, "Ligation–independent cloning of PCR products (LIC–PCR)", Nucleic. Acids Res. 18:6069–6074.
Berkner, 1988, "Development of adenovirus vectors for the expression of heterologous genes", Biotechniques 6:616–629.
Black et al., 1986, "Genomic relationship between capripoxviruses", Virus Res. 5:277–292.
Blackburn et al., 1978, "A tandemly repeated sequence at the termini of the extrachromosomal ribosomal RNA genes in Tetrahymena", J. Mol. Biol. 120:33–53.

(Continued)

Primary Examiner—Karen A. Lacourciere
(74) Attorney, Agent, or Firm—Greenlee, Winner and Sullivan, P.C.

(57) ABSTRACT

A chimeric peptide-nucleic acid construct is disclosed; the peptide portion directs entry of the construct into mitochondria.

22 Claims, 24 Drawing Sheets

OTHER PUBLICATIONS

Capecchi, 1988, "High efficiency transformation by direct microinjection of DNA into cultured mammalian cells" *Cell* 22:479–488.

Chase et al., 1986, "Single–stranded DNA binding proteins required for DNA replication", *Annu. Rev. Biochem.* 55:103–136.

Cohen et al., 1972, "Nonchromosomal antibiotic resistance in bacteria: genetic transformation of *Escherichia coli* by R–Factor DNA", *Proc. Natl. Acad. Sci. U.S.A.* 69:2110–2114.

Dager et al., 1979, "Prolonged incubation in calcium chloride improves the competence of *Escherichia coli* cells", *Gene* 6:23–28.

DePamphilis, 1993, "Eurkaryotic DNA replication: anatomy of an origin", *Annu. Rev. Biochem.* 62:29–63.

Echols et al., 1991, "Fidelity mechanisms in DNA replication", *Annu. Rev. Biochem.* 60:477–511.

Esposito et al., 1985, "Orthopoxyvirus DNA: a comparison of restriction profiles and maps", *Virology* 143:230–251.

Felgner et al., 1987, "Lipofection: a highly efficient, lipid–mediated DNA–transfection procedure", *Proc. Natl. Acad. Sci. U.S.A.* 84:7413–7417.

Horwich et al., 1983, "Molecular cloning of the cDNA coding for rate ornithine transcarbamylase", *Proc. Natl. Acad. Sci. U.S.A.* 80:4258–4262.

K. Geider and H. Hoffman Berling, 1981, "Proteins controlling the helical structure of DNA", *Annu. Rev. Biochem.* 50:233–260.

Klein et al., 1987, "High velocity microprojectiles for delivering nucleic acids into living cells", *Nature* 327:70–73.

Kraus et al., 1985, "A cDNA clone for the precursor of rate mitochondrial ornithine transcarbamylase: comparison of rate and human leader sequences and conservation of catalytic sites", *Nucleic. Acids. Res.* 13:943–952.

Mandel et al., 1970, "Calcium–dependent bacteriophage DNA infection", *J. Mol. Biol.* 53:159–162.

Mannino et al., 1988, "Liposome mediated gene transfer", *Biotechniques* 6:682–690.

Marians, 1992, "Prokaryotic DNA replication", *Annu. Rev. Biochem.* 61:673–719.

Miller, 1989, "Insect baculoviruses: powerful gene expression vectors", *Bioessays* 11:91–95.

Moss et al., 1990, "Product review. New mammalian expression vectors", *Nature* 348:91–92.

Novogrodsky et al., 1966 "The enzymatic phosphorylation of ribonucleic acid and deoxyribonucleic acid, I. Phosphorylation at 5'–hydroxyl termini", *J. Biol. Chem.* 241:2923–2932.

Novogrodsky et al., 1966, "The enzymatic phosphorylation of ribonucleic acid and deoxyribonucleic acid, I. Further properties of the 5'–hydroxyl polynucleotide kinase", *J. Biol. Chem.* 241:2933–2943.

Ogawa et al., 1980, "Discontinuous DNA replication", *Annu. Rev. Biochem.* 49:421–457.

Schnaitman et al., 1968, "Enzymatic properties of the inner and outer membranes of rat liver mitochondria", *J. Cell. Biol.* 38:158–175.

Schnaitman et al., 1967, "The submitochondrial localization of monoamine oxidase. An enzymatic marker for the outer membrane of rat liver mitochondria", *J. Cell Biol.* 32:719–735.

Shigekawa et al., 1988, "Electroporation of eukaryotes and prokaryotes: a general approach to the introduction of macromolecules into cells", *Biotechniques* 6:742–751.

Strauss et al., 1976, "Concatemers of alternating plus and minus strands are intermediates in adenovirus–associated virus DNA synthesis", *Proc. Natl. Acad. Sci. U.S.A.* 73:742–746.

Tattersall et al., 1976, "Rolling hairpin model for the replication of parvovirus and linear chromosomal DNA", *Nature* 263:106–109.

Wallace, 1989, "Report of the committee on human mitochondrial DNA", *Cytogenet. Cell Genet.* 51:612–621.

Wang, 1991, "Eukaryotic DNA polymerases", *Annu. Rev. Biochem.* 60:513–552.

Wang, 1985, "DNA topoisomerases", *Annu. Rev. Biochem.* 54:665–697.

Zimmerman et al., 1983, "Biosynthesis and assembly of nuclear–coded mitochondrial membrane proteins in *Neurospora crassa*", *Methods Enzymol.* 97:275–286.

* cited by examiner

Figure 5b

```
           10         20         30         40         50         60
      CCGCGGTGGC TGGCACGAAA TTGACCAACC CTGGGGTTAG TATAGCTTAG TAAACTTTC
      GGCGCCACCG ACCGTGCTTT AACTGGTTGG GACCCCAATC ATATCGAATC ATTTGAAAG 70         80         90        100        110        120
      GTTTATTGCT AAAGGTTAAT CACTGCTGTT TCCCGTGGGG GTGTGGCTAG CTAAGCGTT
      CAAATAACGA TTTCCAATTA GTGACGACAA AGGGCACCCC CACACCGATC GATTCGCAA 130        140        150        160        170        180
      TTGAGCTGCA TTGCTGCGTG CTTGATGCTT GTTCCTTTTG ATCGTGGTGA TTAGAGGGT
      AACTCGACGT AACGACGCAC GAACTACGAA CAAGGAAAAC TAGCACCACT AATCTCCCA 190        200        210        220        230        240
      GAACTCACTG GAACGGGGAT GCTTGCATGT GTAATCTTAC TAAGAGCTAA AGAAAGGCT
      CTTGAGTGAC CTTGCCCCTA CGAACGTACA CATTAGAATG ATTCTCGATT TCTTTCCGA 250        260        270        280        290        300
      AGGACCAAAC CTATTTGTTT ATGGGGTGAT GTGAGCCCGT CTAAACATTT CAGTGTATT
      TCCTGGTTTG GATAAACAAA TACCCCACTA CACTCGGGCA GATTTGTAAA GTCACATAA 310        320        330        340        350        360
      GCTTTGAGGA GGTAAGCTAC ATAAACTGTG GGGGGTGTCT TTGGGGTTTG TTGGTTCGG
      CGAAACTCCT CCATTCGATG TATTTGACAC CCCCCACAGA AACCCCAAAC AACCAAGCC 370        380        390        400        410        420
      GGTATGGGGT TAGCAGCGGT GTGTGTGTGC TGGGTAGGAT GGGCGGGGGT GTATTGATG
      CCATACCCCA ATCGTCGCCA CACACACACG ACCCATCCTA CCCGCCCCA CATAACTAC 430        440        450        460        470        480
      AGATTAGTAG TATGGGAGTG GGAGGGGAAA ATAATGTGTT AGTTGGGGGG GACTGTTAA
      TCTAATCATC ATACCCTCAC CCTCCCCTTT TATTACACAA TCAACCCCCC CTGACAATT 490        500        510        520        530        540
      AAGTGCATAC CGCCAAAAGA TAAAATTTGA AATCTGGTTA GGCTGGTGTT GGGCCCTTT
      TTCACGTATG GCGGTTTTCT ATTTTAAACT TTAGACCAAT CCGACCACAA CCCGGGAAA 550        560        570        580        590        600
      GTCCCACACC CACCCAAGAA CAGGGTTTGT TAAGATGGCA GAGCCCGGTA TCGCATAAA
      CAGGGTGTGG GTGGGTTCTT GTCCCAAACA ATTCTACCGT CTCGGGCCAT AGCGTATTT 610        620        630        640        650        660
      ACTTAAAACT TTACAGTCAG AGGTTCAATT CCTCTTCTTA ACAACATACC ATGGCCAAC
      TGAATTTTGA AATGTCAGTC TCCAAGTTAA GGAGAAGAAT TGTTGTATGG TACCGGTTG 670        680        690        700        710        720
      CTCCTACTCC TCATTGTACC CATTCTAATC GCAATGGCAT TCCTAATGCT ACCGAACGA
      GAGGATGAGG AGTAACATGG GTAAGATTAG CGTTACCGTA AGGATTACGA TGGCTTGCT 730        740        750        760        770        780
      AAAATTCTAG GCTATATACA ACTACGCAAA GGCCCCAACG TGGTAGGCCC TACGGGCTA
      TTTTAAGATC CGATATATGT TGATGCGTTT CCGGGGTTGC ACCATCCGGG ATGCCCGAT 790        800        810        820        830        840
      CTACAACCCT TCGCTGACGC CATAAAACTC TTCACCAAAG AGCCCCTAAA CCCGCCACA
      GATGTTGGGA AGCGACTGCG GTATTTTGAG AAGTGGTTTC TCGGGGATTT GGGCGGTGT
```

```
          850        860        870        880        890        900
   TCTACCATCA CCCTCTACAT CACCGCCCCG ACCTTAGCTC TCACCATCGC CTTCTACTA
   AGATGGTAGT GGGAGATGTA GTGGCGGGGC TGGAATCGAG AGTGGTAGCG GAAGATGAT 910        920        930        940        950        960
   TGAACCCCCC TCCCCATACC CAACCCCCTG GTCAACCTCA ACCTAGGCCT CTATTTATT
   ACTTGGGGGG AGGGGTATGG GTTGGGGGAC CAGTTGGAGT TGGATCCGGA GATAAATAA 970        980        990       1000       1010       1020
   CTAGCCACCT CTAGCCTAGC CGTTTACTCA ATCCTCTGAT CAGGGTGAGC TCAAACTCA
   GATCGGTGGA GATCGGATCG GCAAATGAGT TAGGAGACTA GTCCCACTCG AGTTTGAGT 1030       1040       1050       1060       1070       1080
   AACTACGCCC TGATCGGCGC ACTGCGAGCA GTAGCCCAAA CAATCTCATA GAAGTCACC
   TTGATGCGGG ACTAGCCGCG TGACGCTCGT CATCGGGTTT GTTAGAGTAT CTTCAGTGG 1090       1100       1110       1120       1130       1140
   CTAGCCATCA TTCTACTATC AACATTACTA ATAAGTGGCT CCTTTAACCT TCCACCCTT
   GATCGGTAGT AAGATGATAG TTGTAATGAT TATTCACCGA GGAAATTGGA AGGTGGGAA 1150       1160       1170       1180       1190       1200
   ATCACAACAC AAGAACACCT CTGATTACTC CTGCCATCAT GACCCTTGGC ATAATATGA
   TAGTGTTGTG TTCTTGTGGA GACTAATGAG GACGGTAGTA CTGGGAACCG TATTATACT 1210       1220       1230       1240       1250       1260
   TTTATCTCCA CACTAGCAGA GACCAACCGA ACCCCCTTCG ACCTTGCCGA GGGGAGTCC
   AAATAGAGGT GTGATCGTCT CTGGTTGGCT TGGGGGAAGC TGGAACGGCT CCCCTCAGG 1270       1280       1290       1300       1310       1320
   GAACTAGTCT CAGGCTTCAA CATCGAATAC GCCGCAGGCC CCTTCGCCCT TTCTTCATA
   CTTGATCAGA GTCCGAAGTT GTAGCTTATG CGGCGTCCGG GGAAGCGGGA AAGAAGTAT 1330       1340       1350       1360       1370       1380
   GCCGAATACA CAAACATTAT TATAATAAAC ACCCTCACCA CTACAATCTT CTAGGAACA
   CGGCTTATGT GTTTGTAATA ATATTATTTG TGGGAGTGGT GATGTTAGAA GATCCTTGT 1390       1400       1410       1420       1430       1440
   ACATATGACG CACTCTCCCC TGAACTCTAC ACAACATATT TTGTCACCAA ACCCTACTT
   TGTATACTGC GTGAGAGGGG ACTTGAGATG TGTTGTATAA AACAGTGGTT TGGGATGAA 1450       1460
   CTAACCTCCC TGTTCTTATG AATTC
   GATTGGAGGG ACAAGAATAC TTAAG
```

Figure 6b
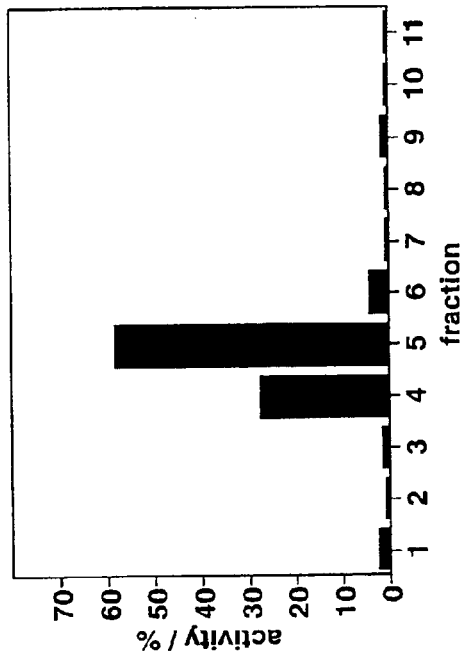
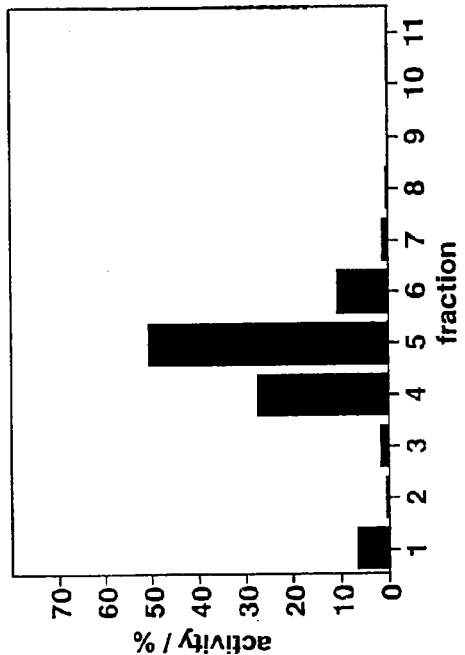
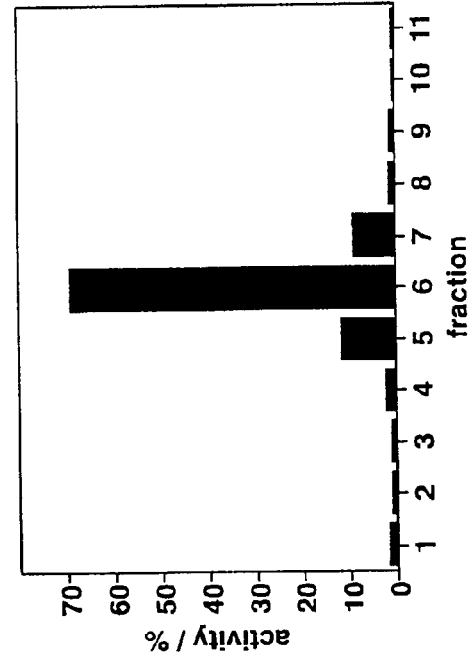
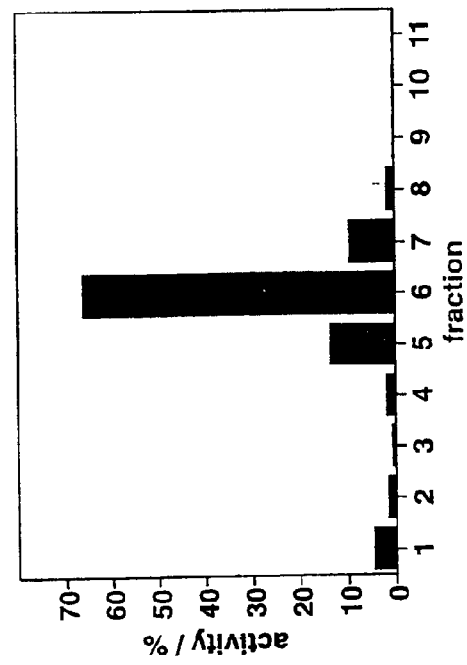

Figure 10

```
            10         20         30         40         50         60
     CTCGAGGGTC TCAGGGGCTA ATAGAAAGGC TAGGACCAAA CCTATTTGTT TATGGGGTGA
     GAGCTCCCAG AGTCCCCGAT TATCTTTCCG ATCCTGGTTT GGATAAACAA ATACCCCACT 70         80         90        100        110        120
     TGTGAGCCCG TCTAAACATT TTCAGTGTAT TGCTTTGAGG AGGTAAGCTA CATAAACTGT
     ACACTCGGGC AGATTTGTAA AAGTCACATA ACGAAACTCC TCCATTCGAT GTATTTGACA 130        140        150        160        170        180
     GGGGGGTGTC TTTGGGGTTT GGTTGGTTCG GGGTATGGGG TTAGCAGCGG TGTGTGTGTG
     CCCCCCACAG AAACCCCAAA CCAACCAAGC CCCATACCCC AATCGTCGCC ACACACACAC 190        200        210        220        230        240
     CTGGGTAGGA TGGGCGGGGG TTGTATTGAT GAGATTAGTA GTATGGGAGT GGGAGGGGAA
     GACCCATCCT ACCCGCCCCC AACATAACTA CTCTAATCAT CATACCCTCA CCCTCCCCTT 250        260        270        280        290        300
     AATAATGTGT TAGTTGGGGG GTGACTGTTA AAAGTGCATA CCGCCAAAAG ATAAAATTTG
     TTATTACACA ATCAACCCCC CACTGACAAT TTTCACGTAT GGCGGTTTTC TATTTTAAAC 310        320        330        340        350        360
     AAATCTGGTT AGGCTGGTGT TAGGGTTCTT TGTTTTTGGG GTTTGGCAGA GATGTGTTTA
     TTTAGACCAA TCCGACCACA ATCCCAAGAA ACAAAAACCC CAAACCGTCT CTACACAAAT 370        380        390        400        410        420
     AGTGCTGTGG CCAGAAGCGG GGGAGGGGGG GTTTGGTGGA AATTTTTTGT TATGATGTCT
     TCACGACACC GGTCTTCGCC CCCTCCCCCC CAAACCACCT TTAAAAAACA ATACTACAGA 430        440        450        460        470        480
     GTGTGGAAAG TGGCTGTGCA GACATTCAAT TGTTATTATT ATGTCCTACA AGCATTAATT
     CACACCTTTC ACCGACACGT CTGTAAGTTA ACAATAATAA TACAGGATGT TCGTAATTAA 490        500        510        520        530        540
     AATTAACACA CTTTAGTAAG TATGTTCGCC TGTAATATTG AACGTAGGTG CGATAAATAA
     TTAATTGTGT GAAATCATTC ATACAAGCGG ACATTATAAC TTGCATCCAC GCTATTTATT 550        560        570        580        590        600
     TAGGATGAGG CAGGAATCAA AGACAGATAC TGCGACATAG GGTGCTCCGG CTCCAGCGTC
     ATCCTACTCC GTCCTTAGTT TCTGTCTATG ACGCTGTATC CCACGAGGCC GAGGTCGCAG 610        620        630        640        650        660
     TCGCAATGCT ATCGCGTGCA TACCCCCCAG ACGAAAATAC CAAATGCATG GAGAGCTCCC
     AGCGTTACGA TAGCGCACGT ATGGGGGGTC TGCTTTTATG GTTTACGTAC CTCTCGAGGG 670        680        690        700        710        720
     GTGAGTGGTT AATAGGGTGA TAGACCTGTG ATCCATCGTG ATGTCTTATT TAAGGGGAAC
     CACTCACCAA TTATCCCACT ATCTGGACAC TAGGTAGCAC TACAGAATAA ATTCCCCTTG 730        740        750        760        770        780
     GTGTGGGCTA TTTAGGCTTT ATGACCCTGA AGTAGGAACC AGATGTCGGA TACAGTTCAC
     CACACCCGAT AAATCCGAAA TACTGGGACT TCATCCTTGG TCTACAGCCT ATGTCAAGTG
```

```
              790        800        810        820        830        840
       TTTAGCTACC CCCAAGTGTT ATGGGCCCGG AGCGAGGAGA GTAGCACTCT TGTGCGGGAT
       AAATCGATGG GGGTTCACAA TACCCGGGCC TCGCTCCTCT CATCGTGAGA ACACGCCCTA 850        860        870        880        890        900
       ATTGATTTCA CGGAGGATGG TGGTCAAGGG ACCCCTATCT GAGGGGGGTC ATCCATGGGG
       TAACTAAAGT GCCTCCTACC ACCAGTTCCC TGGGGATAGA CTCCCCCCAG TAGGTACCCC 910        920        930        940        950        960
       ACGAGAAGGG ATTTGACTGT AATGTGCTAT GTACGGTAAA TGGCTTTATG TACTATGTAC
       TGCTCTTCCC TAAACTGACA TTACACGATA CATGCCATTT ACCGAAATAC ATGATACATG 970        980        990       1000       1010       1020
       TGTTAAGGGT GGGTAGGTTT GTTGGTATCC TAGTGGGTGA GGGGTGGCTT TGGAGTTGCA
       ACAATTCCCA CCCATCCAAA CAACCATAGG ATCACCCACT CCCCACCGAA ACCTCAACGT 1030       1040       1050       1060       1070       1080
       GTTGATGTGT GATAGTTGAG GGTTGATTGC TGTACTTGCT TGTAAGCATG GGGAGGGGGT
       CAACTACACA CTATCAACTC CCAACTAACG ACATGAACGA ACATTCGTAC CCCTCCCCCA 1090       1100       1110       1120       1130       1140
       TTTGATGTGG ATTGGGTTTT TATGTACTAC AGGTGGTCAA GTATTTATGG TACCGTACAA
       AAACTACACC TAACCCAAAA ATACATGATG TCCACCAGTT CATAAATACC ATGGCATGTT 1150       1160       1170       1180       1190       1200
       TATTCATGGT GGCTGGCAGT AATGTACGAA ATACATAGCG GTTGTTGATG GGTGAGTCAA
       ATAAGTACCA CCGACCGTCA TTACATGCTT TATGTATCGC CAACAACTAC CCACTCAGTT 1210       1220       1230       1240       1250       1260
       TACTTGGGTG GTACCCAAAT CTGCTTCCCC ATGAAAGAAC AGAGAATAGT TTAAATTAGA
       ATGAACCCAC CATGGGTTTA GACGAAGGGG TACTTTCTTG TCTCTTATCA AATTTAATCT 1270       1280       1290       1300       1310       1320
       ATCTTAGCTT TGGGTGCTAA TGGTGGAGTT AAAGACTTTT TCTCTGATTT GTCCTTGGAA
       TAGAATCGAA ACCCACGATT ACCACCTCAA TTTCTGAAAA AGAGACTAAA CAGGAACCTT 1330       1340       1350       1360       1370       1380
       AAAGGTTTTC ATCTCCGGTT TACAAGACTG GTGTATTAGC TGCAGATATC GCGAAGCTTA
       TTTCCAAAAG TAGAGGCCAA ATGTTCTGAC CACATAATCG ACGTCTATAG CGCTTCGAAT 1390       1400       1410       1420       1430       1440
       AGGCGCCTCA GGTCACCATA TGATCATTTG TTAAGATGGC AGAGCCCGGT AATCGCATAA
       TCCGCGGAGT CCAGTGGTAT ACTAGTAAAC AATTCTACCG TCTCGGGCCA TTAGCGTATT

1450
       AATGAGACCG GATCC
       TTACTCTGGC CTAGG
```

Figure 12

```
           10         20         30         40         50         60
     CTCGAGGGTC TCAGGGGCTA ATAGAAAGGC TAGGACCAAA CCTATTTGTT TATGGGGTGA
     GAGCTCCCAG AGTCCCCGAT TATCTTTCCG ATCCTGGTTT GGATAAACAA ATACCCCACT 70         80         90        100        110        120
     TGTGAGCCCG TCTAAACATT TTCAGTGTAT TGCTTTGAGG AGGTAAGCTA CATAAACTGT
     ACACTCGGGC AGATTTGTAA AAGTCACATA ACGAAACTCC TCCATTCGAT GTATTTGACA 130        140        150        160        170        180
     GGGGGGTGTC TTTGGGGTTT GGTTGGTTCG GGGTATGGGG TTAGCAGCGG TGTGTGTGTG
     CCCCCCACAG AAACCCCAAA CCAACCAAGC CCCATACCCC AATCGTCGCC ACACACACAC 190        200        210        220        230        240
     CTGGGTAGGA TGGGCGGGGG TTGTATTGAT GAGATTAGTA GTATGGGAGT GGGAGGGGAA
     GACCCATCCT ACCCGCCCCC AACATAACTA CTCTAATCAT CATACCCTCA CCCTCCCCTT 250        260        270        280        290        300
     AATAATGTGT TAGTTGGGGG GTGACTGTTA AAAGTGCATA CCGCCAAAAG ATAAAATTTG
     TTATTACACA ATCAACCCCC CACTGACAAT TTTCACGTAT GGCGGTTTTC TATTTTAAAC 310        320        330        340        350        360
     AAATCTGGTT AGGCTGGTGT TAGGGTTCTT TGTTTTTGGG GTTTGGCAGA GATGTGTTTA
     TTTAGACCAA TCCGACCACA ATCCCAAGAA ACAAAAACCC CAAACCGTCT CTACACAAAT 370        380        390        400        410        420
     AGTGCTGTGG CCAGAAGCGG GGGAGGGGGG GTTTGGTGGA AATTTTTTGT TATGATGTCT
     TCACGACACC GGTCTTCGCC CCCTCCCCCC CAAACCACCT TTAAAAAACA ATACTACAGA 430        440        450        460        470        480
     GTGTGGAAAG TGGCTGTGCA GACATTCAAT TGTTATTATT ATGTCCTACA AGCATTAATT
     CACACCTTTC ACCGACACGT CTGTAAGTTA ACAATAATAA TACAGGATGT TCGTAATTAA 490        500        510        520        530        540
     AATTAACACA CTTTAGTAAG TATGTTCGCC TGTAATATTG AACGTAGGTG CGATAAATAA
     TTAATTGTGT GAAATCATTC ATACAAGCGG ACATTATAAC TTGCATCCAC GCTATTTATT 550        560        570        580        590        600
     TAGGATGAGG CAGGAATCAA AGACAGATAC TGCGACATAG GGTGCTCCGG CTCCAGCGTC
     ATCCTACTCC GTCCTTAGTT TCTGTCTATG ACGCTGTATC CCACGAGGCC GAGGTCGCAG 610        620        630        640        650        660
     TCGCAATGCT ATCGCGTGCA TACCCCCAG ACGAAAATAC CAAATGCATG GAGAGCTCCC
     AGCGTTACGA TAGCGCACGT ATGGGGGTC TGCTTTTATG GTTTACGTAC CTCTCGAGGG 670        680        690        700        710        720
     GTGAGTGGTT AATAGGGTGA TAGACCTGTG ATCCATCGTG ATGTCTTATT TAAGGGGAAC
     CACTCACCAA TTATCCCACT ATCTGGACAC TAGGTAGCAC TACAGAATAA ATTCCCCTTG 730        740        750        760        770        780
     GTGTGGGCTA TTTAGGCTTT ATGACCCTGA AGTAGGAACC AGATGTCGGA TACAGTTCAC
     CACACCCGAT AAATCCGAAA TACTGGGACT TCATCCTTGG TCTACAGCCT ATGTCAAGTG 790        800        810        820        830        840
     TTTAGCTACC CCCAAGTGTT ATGGGCCCGG AGCGAGGAGA GTAGCACTCT TGTGCGGGAT
     AAATCGATGG GGGTTCACAA TACCCGGGCC TCGCTCCTCT CATCGTGAGA ACACGCCCTA
```

```
           850        860        870        880        890        900
      ATTGATTTCA CGGAGGATGG TGGTCAAGGG ACCCCTATCT GAGGGGGGTC ATCCATGGGG
      TAACTAAAGT GCCTCCTACC ACCAGTTCCC TGGGGATAGA CTCCCCCCAG TAGGTACCCC 910        920        930        940        950        960
      ACGAGAAGGG ATTTGACTGT AATGTGCTAT GTACGGTAAA TGGCTTTATG TACTATGTAC
      TGCTCTTCCC TAAACTGACA TTACACGATA CATGCCATTT ACCGAAATAC ATGATACATG 970        980        990       1000       1010       1020
      TGTTAAGGGT GGGTAGGTTT GTTGGTATCC TAGTGGGTGA GGGGTGGCTT TGGAGTTGCA
      ACAATTCCCA CCCATCCAAA CAACCATAGG ATCACCCACT CCCCACCGAA ACCTCAACGT 1030       1040       1050       1060       1070       1080
      GTTGATGTGT GATAGTTGAG GGTTGATTGC TGTACTTGCT TGTAAGCATG GGGAGGGGGT
      CAACTACACA CTATCAACTC CCAACTAACG ACATGAACGA ACATTCGTAC CCCTCCCCCA 1090       1100       1110       1120       1130       1140
      TTTGATGTGG ATTGGGTTTT TATGTACTAC AGGTGGTCAA GTATTTATGG TACCGTACAA
      AAACTACACC TAACCCAAAA ATACATGATG TCCACCAGTT CATAAATACC ATGGCATGTT 1150       1160       1170       1180       1190       1200
      TATTCATGGT GGCTGGCAGT AATGTACGAA ATACATAGCG GTTGTTGATG GGTGAGTCAA
      ATAAGTACCA CCGACCGTCA TTACATGCTT TATGTATCGC CAACAACTAC CCACTCAGTT 1210       1220       1230       1240       1250       1260
      TACTTGGGTG GTACCCAAAT CTGCTTCCCC ATGAAAGAAC AGAGAATAGT TTAAATTAGA
      ATGAACCCAC CATGGGTTTA GACGAAGGGG TACTTTCTTG TCTCTTATCA AATTTAATCT 1270       1280       1290       1300       1310       1320
      ATCTTAGCTT TGGGTGCTAA TGGTGGAGTT AAAGACTTTT TCTCTGATTT GTCCTTGGAA
      TAGAATCGAA ACCCACGATT ACCACCTCAA TTTCTGAAAA AGAGACTAAA CAGGAACCTT 1330       1340       1350       1360       1370       1380
      AAAGGTTTTC ATCTCCGGTT TACAAGACTG GTGTATTAGC TGCAGATATC GCGAAGCTTG
      TTTCCAAAAG TAGAGGCCAA ATGTTCTGAC CACATAATCG ACGTCTATAG CGCTTCGAAC 1390       1400       1410       1420       1430       1440
      TAACATGGTA AGTGTACTGG AAAGTGCACT TGGACGAACC AGAGTGTAGC TTAACACAAA
      ATTGTACCAT TCACATGACC TTTCACGTGA ACCTGCTTGG TCTCACATCG AATTGTGTTT 1450       1460       1470       1480       1490       1500
      GCACCCAACT TACACTTAGG AGATTTCAAC TTAACTTGAC CGCTCTGAGC TAAACCTAGC
      CGTGGGTTGA ATGTGAATCC TCTAAAGTTG AATTGAACTG GCGAGACTCG ATTTGGATCG 1510       1520       1530       1540       1550       1560
      CCCAAACCCA CTCCACCTTA CTACCAGACA ACCTTAGCCA AACCATTTAC CCAAATAAAG
      GGGTTTGGGT GAGGTGGAAT GATGGTCTGT TGGAATCGGT TTGGTAAATG GGTTTATTTC 1570       1580       1590       1600       1610       1620
      TATAGGCGAT AGAAATTGAA ACCTGGCGCA ATAGATATAG TACCGCAAGG GAAAGATGAA
      ATATCCGCTA TCTTTAACTT TGGACCGCGT TATCTATATC ATGGCGTTCC CTTTCTACTT 1630       1640       1650       1660       1670       1680
      AAATTATAAC CAAGCATAAT ATAGCAAGGA CTAACCCCTA TACCTTCTGC ATAATGAATT
      TTTAATATTG GTTCGTATTA TATCGTTCCT GATTGGGGAT ATGGAAGACG TATTACTTAA
```

```
         1690       1700       1710       1720       1730       1740
    AACTAGAAAT AACTTTGCAA GGAGAGCCAA AGCTAAGACC CCCGAAACCA GACGAGCTAC
    TTGATCTTTA TTGAAACGTT CCTCTCGGTT TCGATTCTGG GGGCTTTGGT CTGCTCGATG 1750       1760       1770       1780       1790       1800
    CTAAGAACAG CTAAAAGAGC ACACCCGTCT ATGTAGCAAA ATAGTGGGAA GATTTATAGG
    GATTCTTGTC GATTTTCTCG TGTGGGCAGA TACATCGTTT TATCACCCTT CTAAATATCC 1810       1820       1830       1840       1850       1860
    TAGAGGCGAC AAACCTACCG AGCCTGGTGA TAGCTGGTTG TCCAAGATAG AATCTTAGTT
    ATCTCCGCTG TTTGGATGGC TCGGACCACT ATCGACCAAC AGGTTCTATC TTAGAATCAA 1870       1880       1890       1900       1910       1920
    CAACTTTAAA TTTGCCCACA GAACCCTCTA AATCCCCTTG TAAATTTAAC TGTTAGTCCA
    GTTGAAATTT AAACGGGTGT CTTGGGAGAT TTAGGGGAAC ATTTAAATTG ACAATCAGGT 1930       1940       1950       1960       1970       1980
    AAGAGGAACA GCTCTTTGGA CACTAGGAAA AAACCTTGTA GAGAGAGTAA AAAATTTAAC
    TTCTCCTTGT CGAGAAACCT GTGATCCTTT TTTGGAACAT CTCTCTCATT TTTTAAATTG 1990       2000       2010       2020       2030       2040
    ACCCATAGTA GGCCTAAAAG CAGCCACCAA TTAAGAAAGC GTTCAAGCTC AACACCCACT
    TGGGTATCAT CCGGATTTTC GTCGGTGGTT AATTCTTTCG CAAGTTCGAG TTGTGGGTGA 2050       2060       2070       2080       2090       2100
    ACCTAAAAAA TCCCAAACAT ATAACTGAAC TCCTCACACC CAATTGGACC AATCTATCAC
    TGGATTTTTT AGGGTTTGTA TATTGACTTG AGGAGTGTGG GTTAACCTGG TTAGATAGTG 2110       2120       2130       2140       2150       2160
    CCTATAGAAG AACTAATGTT AGTATAAGTA ACATGAAAAC ATTCTCCTCC GCATAAGCCT
    GGATATCTTC TTGATTACAA TCATATTCAT TGTACTTTTG TAAGAGGAGG CGTATTCGGA 2170       2180       2190       2200       2210       2220
    GCGTCAGATT AAAACACTGA ACTGACAATT AACAGCCCAA TATCTACAAT CAACCAACAA
    CGCAGTCTAA TTTTGTGACT TGACTGTTAA TTGTCGGGTT ATAGATGTTA GTTGGTTGTT 2230       2240       2250       2260       2270       2280
    GTCATTATTA CCCTCACTGT CAACCCAACA CAGGCATGCT CATAAGGAAA GGTTAAAAAA
    CAGTAATAAT GGGAGTGACA GTTGGGTTGT GTCCGTACGA GTATTCCTTT CCAATTTTTT 2290       2300       2310       2320       2330       2340
    AGTAAAAGGA ACTCGGCAAA TCTTACCCCG CCTGTTTACC AAAAACATCA CCTCTAGCAT
    TCATTTTCCT TGAGCCGTTT AGAATGGGGC GGACAAATGG TTTTTGTAGT GGAGATCGTA 2350       2360       2370       2380       2390       2400
    CACCAGTATT AGAGGCACCG CCTGCCCAGT GACACATGTT TAACGGCCGC GGTACCCTAA
    GTGGTCATAA TCTCCGTGGC GGACGGGTCA CTGTGTACAA ATTGCCGGCG CCATGGGATT 2410       2420       2430       2440       2450       2460
    CCGTGCAAAG GTAGCATAAT CACTTGTTCC TTAAATAGGG ACCTGTATGA ATGGCTCCAC
    GGCACGTTTC CATCGTATTA GTGAACAAGG AATTTATCCC TGGACATACT TACCGAGGTG 2470       2480       2490       2500       2510       2520
    GAGGGTTCAG CTGTCTCTTA CTTTTAACCA GTGAAATTGA CCTGCCCGTG AAGAGGCGGG
    CTCCCAAGTC GACAGAGAAT GAAAATTGGT CACTTTAACT GGACGGGCAC TTCTCCGCCC
```

```
           2530       2540       2550       2560       2570       2580
      CATAACACAG CAAGACGAGA AGACCCTATG GAGCTTTAAT TTATTAATGC AAACAGTACC
      GTATTGTGTC GTTCTGCTCT TCTGGGATAC CTCGAAATTA AATAATTACG TTTGTCATGG 2590       2600       2610       2620       2630       2640
      TAACAAACCC ACAGGTCCTA AACTACCAAA CCTGCATTAA AAATTTCGGT TGGGGCGACC
      ATTGTTTGGG TGTCCAGGAT TTGATGGTTT GGACGTAATT TTTAAAGCCA ACCCCGCTGG 2650       2660       2670       2680       2690       2700
      TCGGAGCAGA ACCCAACCTC CGAGCAGTAC ATGCTAAGAC TTCACCAGTC AAAGCGAACT
      AGCCTCGTCT TGGGTTGGAG GCTCGTCATG TACGATTCTG AAGTGGTCAG TTTCGCTTGA 2710       2720       2730       2740       2750       2760
      ACTATACTCA ATTGATCCAA TAACTTGACC AACGGAACAA GTTACCCTAG GGATAACAGC
      TGATATGAGT TAACTAGGTT ATTGAACTGG TTGCCTTGTT CAATGGGATC CCTATTGTCG 2770       2780       2790       2800       2810       2820
      GCAATCCTAT TCTAGAGTCC ATATCAACAA TAGGGTTTAC GACCTCGATG TTGGATCAGG
      CGTTAGGATA AGATCTCAGG TATAGTTGTT ATCCCAAATG CTGGAGCTAC AACCTAGTCC 2830       2840       2850       2860       2870       2880
      ACATCCCGAT GGTGCAGCCG CTATTAAAGG TTCGTTTGTT CAACGATTAA AGTCCTACGT
      TGTAGGGCTA CCACGTCGGC GATAATTTCC AAGCAAACAA GTTGCTAATT TCAGGATGCA 2890       2900       2910       2920       2930       2940
      GATCTGAGTT CAGACCGGAG TAATCCAGGT CGGTTTCTAT CTACCTTCAA ATTCCTCCCT
      CTAGACTCAA GTCTGGCCTC ATTAGGTCCA GCCAAAGATA GATGGAAGTT TAAGGAGGGA 2950       2960       2970       2980       2990       3000
      GTACGAAAGG ACAAGAGAAA TAAGGCCTAC TTCACAAAGC GCCTTCCCCC GTAAATGATA
      CATGCTTTCC TGTTCTCTTT ATTCCGGATG AAGTGTTTCG CGGAAGGGGG CATTTACTAT 3010       3020       3030       3040       3050       3060
      TCATCTCAAC TTAGTATTAT ACCCACACCC ACCCAAGAAC AGGGTTTGTT AAGATGGCAG
      AGTAGAGTTG AATCATAATA TGGGTGTGGG TGGGTTCTTG TCCCAAACAA TTCTACCGTC 3070       3080       3090       3100       3110       3120
      AGCCCGGTAA TCGCATAAAA CTTAAAACTT TACAGTCAGA GGTTCAATTC CTCTTCTTAA
      TCGGGCCATT AGCGTATTTT GAATTTTGAA ATGTCAGTCT CCAAGTTAAG GAGAAGAATT 3130       3140       3150       3160       3170       3180
      CAACATACCC ATGGCCAACC TCCTACTCCT CATTGTACCC ATTCTAATCG CAATGGCTGA
      GTTGTATGGG TACCGGTTGG AGGATGAGGA GTAACATGGG TAAGATTAGC GTTACCGACT 3190       3200       3210       3220       3230
      TCATTTGTTA AGATGGCAGA GCCCGGTAAT CGCATAAAAT GAGACCGGAT CC
      AGTAAACAAT TCTACCGTCT CGGGCCATTA GCGTATTTTA CTCTGGCCTA GG
```

Figure 15
15a
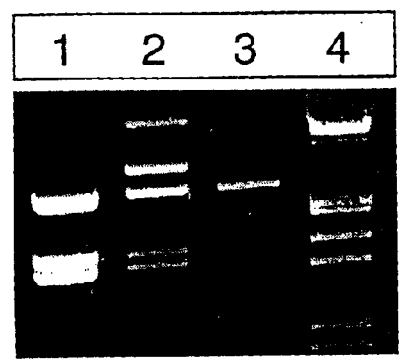
15b
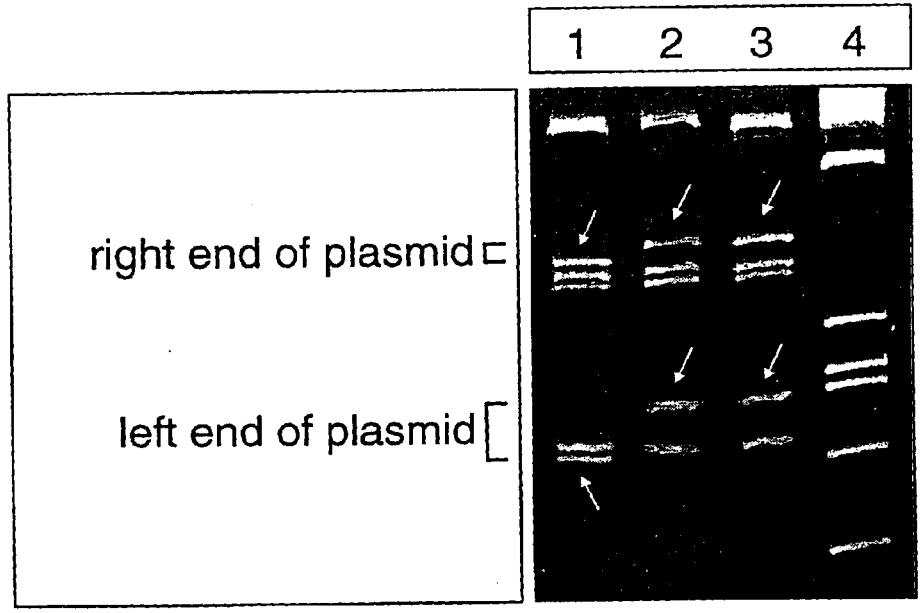

CHIMERICAL PEPTIDE-NUCLEIC ACID FRAGMENT, PROCESS FOR PRODUCING THE SAME AND ITS FOR APPROPRIATELY INTRODUCING NUCLEIC ACIDS INTO CELL ORGANELLES AND CELLS

CROSS REFERENCE TO RELATED APPLICATIONS

This application is a national application filed under 35 U.S.C. 371, based on International Application PCT/DE95/00775, filed Jun. 16, 1995, which application claims benefit of German Patent Application DE P 44 21 079.5, filed Jun. 16, 1994.

BACKGROUND OF THE INVENTION

This invention relates to a chimeric peptide-nucleic acid fragment, the process for producing the same and its use for appropriately introducing nucleic acids into cell organelles and cells.

It is known that cellular membrane systems are largely impermeable to nucleic acids. However, cell membranes can be overcome very efficiently by physical processes (transformation) and biological processes (infection). Transformation, i.e. the direct absorption of the naked nucleic acid by the cell, is preceded by cell treatment. There are various methods available for the production of these 'competent cells'. Most processes are based on the observations made by Mandel and Higa (M. Mandel et al., (1970), "Calcium-dependent bacteriophage DNA infection", J. Mol. Biol. 53: 159–162), who could show for the first time that the yields resulting from the absorption of lambda-DNA by bacteria can be increased fundamentally in the presence of calcium chloride. This method is also used successfully for the first time by Cohen et al. (S. N. Cohen et al. (1972), "Nonchromosomal antibiotic resistance in bacteria: genetic transformation of Escherichia coli by R-factor DNA", Proc. Natl. Acad. Sci. U.S.A. 69: 2110–2114) for plasmid DNA and was improved by many modifications (M. Dagert et al. (1979), "Prolonged incubation in calcium chloride improves the competence of Escherichia coli cells", Gene 6: 23–28). Another transformation method is based on the observation that high-frequency alternating fields may break up cell membranes (electroporation). This technique can be used to introduce naked DNA into not only prokaryotic cells but also eukaryotic cell systems (K. Shigekawa et al. (1988), "Electroporation of eukaryotes and prokaryotes: a general approach to the introduction of macromolecules into cells", Biotechniques 6: 742–751). Two very gentle methods of introducing DNA into eukaryotic cells were developed by Capecchi (M. R. Capecchi (1980), "High efficiency transformation by direct microinjection of DNA into cultured mammalian cells" Cell 22: 479–488) and Klein et al. (T. M. Klein et al. (1987), "High velocity microprojectiles for delivering nucleic acids into living cells", Nature 327: 70–73): They are based on the direct injection of the DNA into the individual cell (microinjection), on the one hand, and on the bombardment of a cell population with microprojectiles consisting of tungsten, to the surface of which the corresponding nucleic acid was bound ('shotgun'). The biological infection methods proved their value parallel to the physical transformation of cells. They include particularly the highly efficient viral introduction of nucleic acids into cells (K. L. Berkner (1988), "Development of adenovirus vectors for the expression of heterologous genes", Biotechniques 6: 616–629; L. K. Miller (1989), "Insect baculoviruses: powerful gene expression vectors", Bioessays 11: 91–95; B. Moss et al. (1990), "Product review. New mammalian expression vectors", Nature 348: 91–92) and the liposome mediated lipofection (R. J. Mannino et al. (1988), "Liposome mediated gene transfer", Biotechniques 6: 682–690; P. L. Felgner et al. (1987), "Lipofection: a highly efficient, lipid-mediated DNA-transfection procedure", Proc. Natl. Acad. Sci. U.S.A. 84: 7413–7417). All methods described so far deal with the overcoming of the prokaryotic or eukaryotic plasma membrane by naked or packaged nucleic acids. While the site of action is reached already when the nucleic acid are introduced into the prokaryotic cell, further biochemical processes take place in a compartmentalized eukaryotic cell, which support the penetration of the nucleic acid into the nucleus under certain conditions (e.g. viral route of infection in the case of HIV). Analogous infective processes in which exogenous nucleic acids are actively introduced into other cell organelles (e.g. into mitochondria) have not been described so far.

In addition to the introduction of the nucleic acid into the cell and cell organelle, respectively, the transcription and above all the replication of the introduced nucleic acid play a decisive part. In this connection, it is known that the DNA molecules may have a special property which permits duplication in a cell under certain conditions. A special structural element, the origin of the DNA replication (ori, origin), adds thereto. Its presence provides the ability of DNA replication (K. J. Marians (1992), "Prokaryotic DNA replication", Annu. Rev. Biochem. 61: 673–719; M. L. DePamphilis (1993), "Eukaryotic DNA replication: anatomy of an origin", Annu. Rev. Biochem. 62: 29–63; H. Echols and M. F. Goodman (1991), "Fidelity mechanisms in DNA replication", Annu. Rev. Biochem. 60: 477–511). The strictly controlled process of DNA replication starts in E. coli e.g. when a protein is bound (K. Geider and H. Hoffmann Berling (1981), "Proteins controlling the helical structure of DNA", Annu. Rev. Biochem. 50: 233–260) to the highly specific initiation site thus defining the starting point of a specific RNA polymerase (primase). It synthesizes a short RNA strand (~10 nucleotides, 'primer') which is complementary to one of the DNA template strands. The 3' hydroxyl group of the terminal ribonucleotide of this RNA chain serves as 'primer' for the synthesis of new DNA by a DNA polymerase. DNA-untwisting proteins unwind the DNA double helix (J. C. Wang (1985), "DNA topoisomerases", Annu. Rev. Biochem. 54: 665–697). The separated individual strands are stabilized by DNA-binding proteins as regards their conformation (J. W. Chase and K. R. Williams (1986), "Single-stranded DNA binding proteins required for DNA replication", Annu. Rev. Biochem 55: 103–136) to enable proper functioning of the DNA polymerases (T. S. Wang (1991), "Eukaryotic DNA polymerases", Annu. Rev. Biochem. 60: 513–552). A multienzyme complex, the holoenzyme of DNA-polymerase-III, synthesizes the majority of the new DNA. The RNA portion of the chimeric RNA-DNA molecule is then split off the DNA polymerase III. The removal of the RNA from the newly formed DNA chains creates gaps between the DNA fragments. These gaps are filled by DNA-polymerase I which can newly synthesize DNA from a single-stranded template. While one of the two newly synthesized DNA strands is synthesized continuously (5'–3' direction, leader strand), Ogawa and Okazaki observed that a majority of the newly synthesized opposite strand (3'–5' direction, delayed strand) was synthesized from short DNA fragments (T. Ogawa and T. Okazaki (1980), "Discontinuous DNA replication", Annu. Rev. Biochem. 49: 421–457). Here, what is called primases initiate the onset of the DNA synthesis of the opposite strand by the synthesis of several RNA primers. When the replication proceeds, these fragments are freed from their RNA primers, the gaps are closed and covalently linked with one another to give extended daughter strands by the DNA ligase. Two chromosomes form after the termination of the replication cycle.

DNA replication is controlled in many plasmids via a replication origin which dispenses with the synthesis of the delayed strand (3'–5' direction) and can initiate the synthesis of two continuous DNA strands bidirectionally (each in the 5'–3' direction along the two templates). The precondition for a complete DNA replication is here the cyclic form of the nucleic acid. It ensures that at the end of the new synthesis of the complementary DNA strands the DNA polymerases return to the starting point again where now ligases guarantee the covalent linkage of the ends of the two newly synthesized daughter strands.

Smallpox viruses represent an interesting form of linear-cyclic nucleic acids: because of what is called 'hairpin loops' at the ends of their linear genomes, they have a cyclic molecule structure while maintaining a predominantly linear conformation (D. N. Black et al. (1986), "Genomic relationship between capripoxviruses", Virus Res. 5: 277–292; J. J. Esposito and J. C. Knight (1985) "*Orthopoxvirus* DNA: a comparison of restriction profiles and maps", Virology 143: 230–251). Covalently closed "hairpin" nucleic acids were not only found in smallpox viruses but also described for the ribosomal RNA from Tetrahymena (E. H. Blackburn and J. G. Gall (1978), "A tandemly repeated sequence at the termini of the extrachromosomal ribosomal RNA genes in Tetrahymena", J. Mol. Biol. 120: 33–53) and the genomes of the parvoviruses (S. E. Straus et al. (1976), "Concatemers of alternating plus and minus strands are intermediates in adenovirus-associated virus DNA synthesis", Proc. Natl. Acad. Sci. U.S.A. 73: 742–746; P. Tattersall and D. C. Ward (1976), "Rolling hairpin model for the replication of parvovirus and linear chromosomal DNA", Nature 263: 106–109).

However, by means of the formerly known plasmids or nucleic acid constructs it is not possible to appropriately introduce nucleic acids into cells or cell organelles via the protein import route. But this is e.g. a precondition for genetically treating changes of the mitochondrial genomes of patients suffering from neuromuscular and neurodegenerative diseases or carrying out an appropriate mutagenesis in mitochondria or other cell organelles.

SUMMARY OF THE INVENTION

It is an object of the present invention to provide methods and compositions for targeting nucleic acids to cells and to particular cellular compartments of eukaryotic cells, especially the mitochondria. The compositions of the present invention are peptide-nucleic acid complexes, in which the peptide and nucleic acid are covalently joined, including linkage via a third "linker" component. It is the peptide portion of the complex which directs the nucleic acid to the cellular compartment of interest. It is preferred that the nucleic acid be such that it can be incorporated as a replicative nucleic acid, and it should have properties which result in controlled transcription and/or replication in cells and in defined targeted (aimed) compartments. Specifically exemplified peptide sequences are given in SEQ ID NO:1 and SEQ ID NO:22.

BRIEF DESCRIPTION OF THE DRAWINGS

The present invention is explained particularly by the figures, wherein:

FIG. 5b shows the sequence of the cloned tRNA$^{Leu\ (UUU)}$ gene. See FIGS. 6a and 6b, SEQ ID NO:7 and SEQ ID NO:8.

FIGS. 6a and 6b show the $^{32}$P radioactivity of the DNA and the enzyme activities for adenylate kinase, cytochrome c oxidase and malate dehydrogenase (y axes) in 11 fractions (x axes) after mitochondria-sucrose gradient density centrifugation. The particular percentage of the total radioactivity/enzyme activity which was plotted against the gradient fraction number is illustrated. ADK: adenylate kinase; COX: cytochrome c oxidase; MDH: malate dehydrogenase.

promoter characterized by the binding sites for the mitochondrial transcription factors and the RNA polymerase; replication origin characterized by what is called 'conserved sequence blocks'; regulation of the DNA replication characterized by the 'TAS' motifs). Since the oligonucleotides contain recognition sequences for the restriction endonucleases Xho I and Pst I, the ends of the amplified nucleic acid can be modified such that they are compatible with a vector arm of pBluescript, on the one hand, and compatible with the hybrid of the oligonucleotides MCS/TTS 1 and 2, on the other hand. In addition to a multiple cloning site, they also comprise a transcription termination sequence which is responsible for the regulated transcription. The ligation product is then transformed into E. coli XL 1. Following the plasmid isolation of insert-carrying E. coli colonies, the nucleic acids were subjected to RFLP and sequence analysis.

Figure 9:
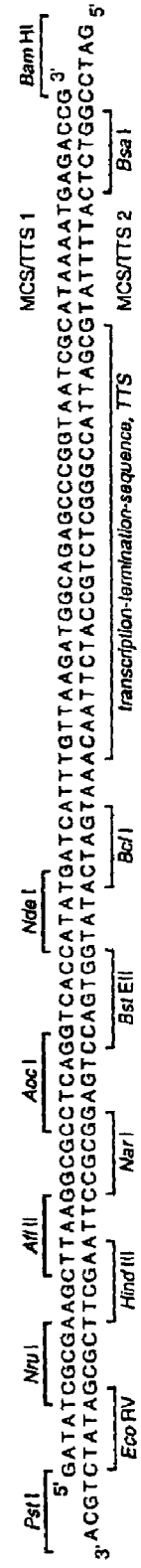

FIG. 9 shows the sequences of the oligonucleotides MCS/ITS 1 and 2. The oligonucleotides MCS 1 and 2 (SEQ ID NOs:9 and 10) were prepared synthetically and comprise recognition sequences for nine different restriction endonucleases as well as a sequence motif which can suppress the transcription bidirectionally. The oligonucleotides are complementary and can thus form a hybrid. The overhanging ends are part of the recognition sequences for the restriction endonucleases Pst I and Bam HI.

FIG. 10 shows the nucleotide sequence of the nucleic acid portion of the peptide-nucleic acid plasmid (plasmid 1). See SEQ ID NOs:11 and 12.

Figure 11:
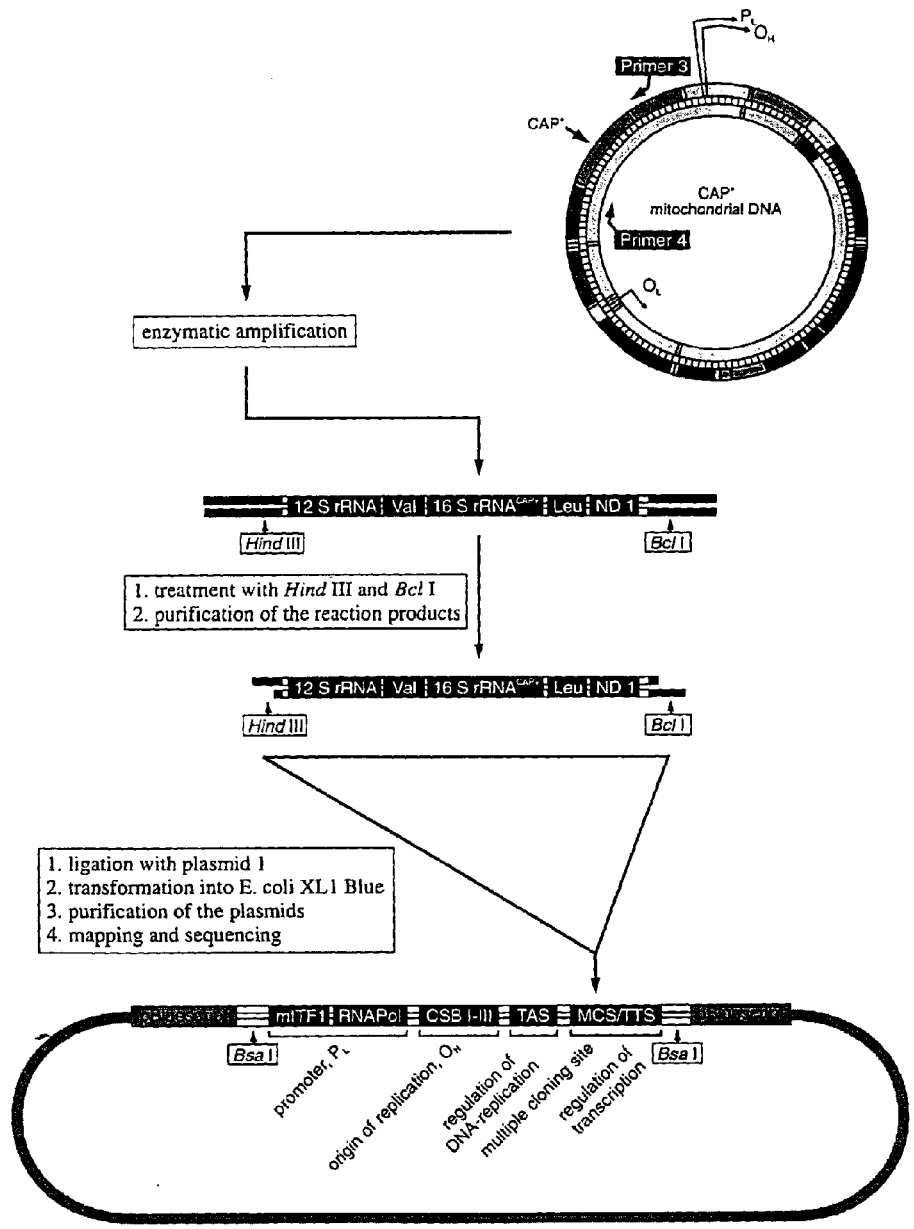

FIG. 11 shows the cloning of the reporter gene into the nucleic acid portion of the peptide-nucleic acid plasmid into pBluescript (plasmid 2). See also SEQ ID NOs:7 AND 8. Using the two oligonucleotides (primers 3 and 4), the gene section of nucleotide 1562 to nucleotide 3359 was amplified enzymatically from a DNA extract of a human CAP-resistant cell line (comprises: part of the 12S rRNA gene, tRNA$^{Val}$ gene, 16S rRNA$^{CAP+}$gene, tRNA$^{Leu}$ gene, part of ND 1 gene). Since the oligonucleotides contain recognition sequences for the restriction endonucleases Hind III and Bcl I, the ends of the amplified nucleic acid can be modified such that they are compatible with the multiple cloning site (MCS) of the peptide-nucleic acid plasmid (plasmid 1). The ligation product is then transformed in E. coli XL 1 Blue. Following the plasmid isolation of insert-carrying E. coli colonies., the nucleic acids were subjected to RFLP and sequence analysis and available for the experiments described herein.

FIG. 12 shows the nucleotide sequence of the nucleic acid portion of the peptide-nucleic acid plasmid including the reporter gene (plasmid 2). See SEQ ID NOs:13 AND 14.

Figure 13:
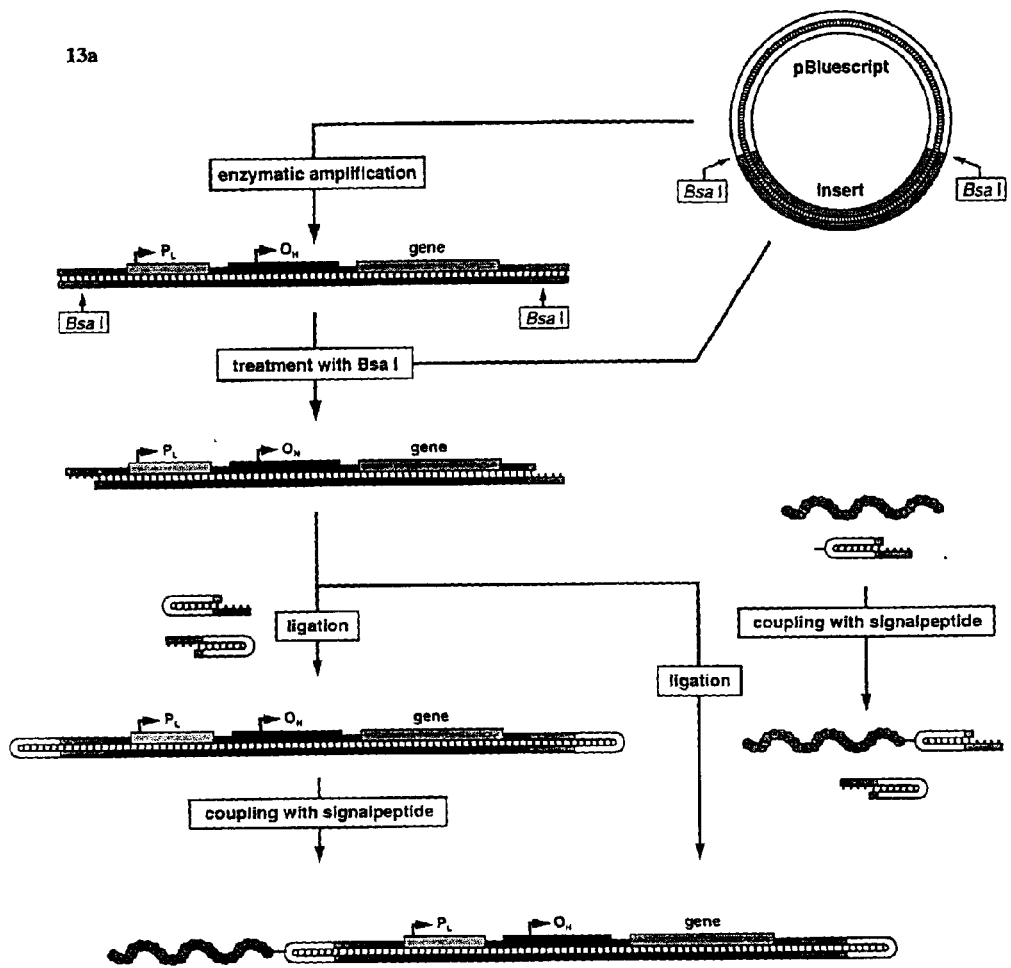

FIG. 13a shows the reaction run of the cyclization, of the nucleic acid portion as well as the conjugation of the nucleic acid portion with a signal peptide. The nucleic acid portion of the peptide-nucleic acid plasmid can be obtained via a plasmid preparation or an enzymatic amplification. In both cases, the treatment with the restriction endonuclease Bsa I results in an intermediate product capable of ligation. It can be reacted directly with the monomerized 'hairpin loops'. The reaction product is freed by an exonuclease III treatment from non-specific (non-cyclic) reaction products and products, is purified and conjugated with the signal peptide via a cross-linker. As an alternative, one of the two 'hairpin loops' can first be conjugated with the signal peptide via a cross-linker before the cyclizing ligation reaction is carried out. A purification of the reaction product follows an exonuclease III treatment here as well.

FIG. 13b shows the structure and sequence of the 'hairpin loop' oligonucleotides HP 1 (SEQ ID NO:2) and 2 (SEQ ID NO:15).

Figure 14:
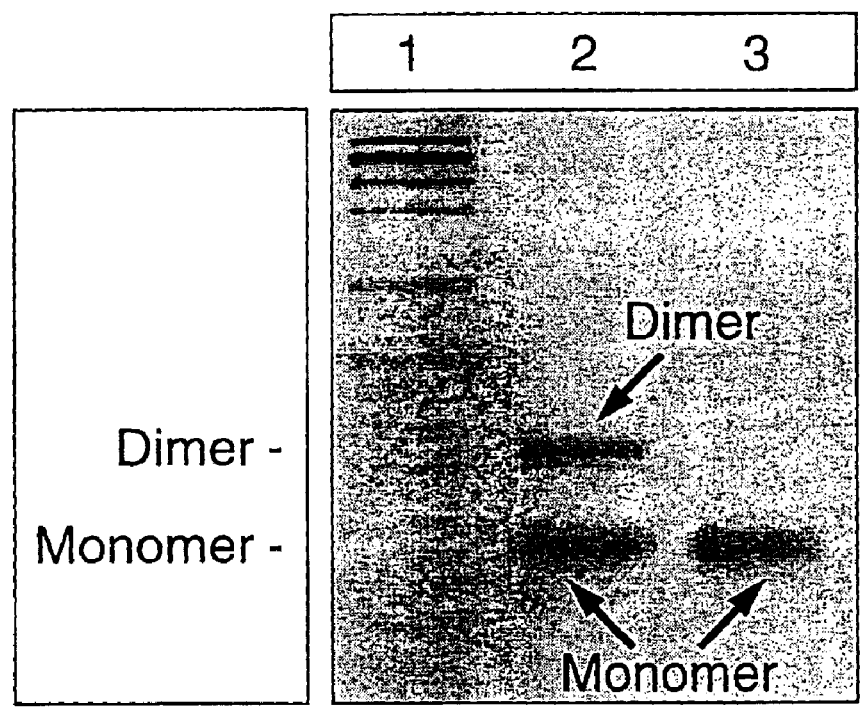

FIG. 14 shows the monomerization of a 'hairpin loop' oligonucleotide. The synthetic 1 and 2 can be monomerized by thermal or alkaline denaturation. This figure shows a standard agarose gel: lane 1, a 'hairpin loop' 'hairpin loops' HP by a thermal or figure shows a molecular weight standard (ΦX 174 RF DNA treated with the restriction endonuclease Hae III), lane 2: HP 1, synthesis product; lane 3: HP 1, thermally monomerized.

FIG. 15a shows a ligation reaction between the nucleic acid portion of the peptide-nucleic acid plasmid (plasmid 2) and the 'hairpin loops' HP 1 and 2. This figure shows a standard agarose gel: lane 1, cloned nucleic acid portion of the peptide-nucleic acid portion in pBluescript treated with the restriction endonuclease Bsa I, lane 2: ligation of the reaction products resulting from lane 1 with the 'hairpin loops' HP 1 and 2; lane 3, treatment of the reaction products resulting from lane 2 with exonuclease III; lane 4, molecular weight standard (λDNA treated with the restriction endonucleases Hind III and Eco RI).

FIG. 15b shows the examination of the purified ligation product by a Mae III-RFLP analysis. This figure illustrates a standard agarose gel: lane 1, enzymatically amplified nucleic acid portion following a Mae III treatment; lane 2: purified ligation product of the enzymatically amplified nucleic acid portion following a Mae III treatment; lane 3: purified product of the plasmid DNA ligation following a Mae III treatment; lane 4, molecular weight standard (ΦX 174 RF DNA treated with the restriction endonuclease Hae III).

Figure 16:
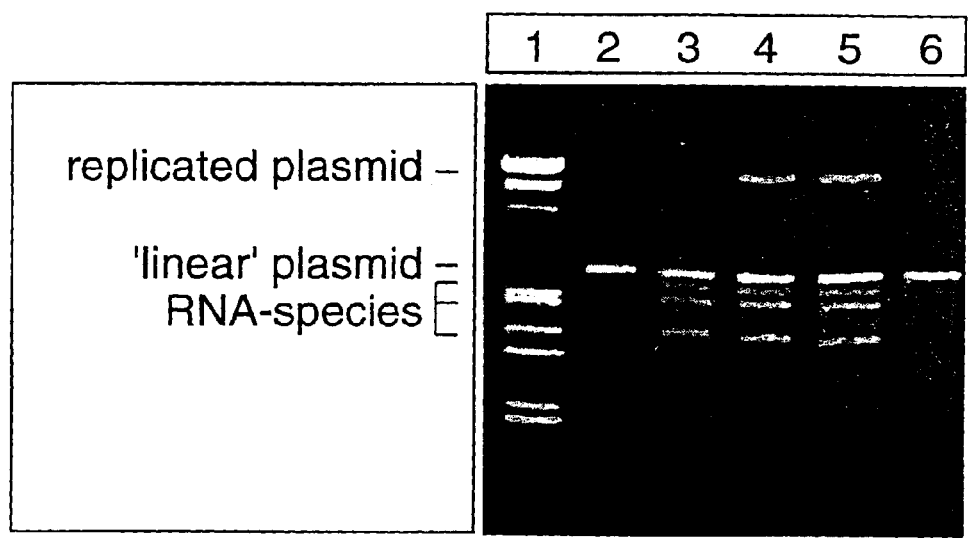

FIG. 16 shows the transcription and replication of the peptide-nucleic acid plasmid. This figure illustrates a standard agarose gel: lane 1, molecular weight standard (λDNA treated with the restriction endonucleases Hind III and Eco RI); lane 2, untreated peptide-nucleic acid plasmid; lane 3: in vitro-obtained transcription products of the peptide-nucleic acid plasmid; lane 4: in vitro-obtained replication and transcription products of the peptide-nucleic acid plasmid; lane 5, in vivo-obtained replication and transcription products of the peptide nucleic acid plasmid; lane 6, untreated peptide-nucleic acid plasmid.

DETAILED DESCRIPTION OF THE INVENTION

It was an object of the present invention to develop a construct on a nucleic acid basis which permits the appropriate introduction of nucleic acids into cell and compartments of eukaryotic cells. Furthermore, a process is to be provided of how this construct can reach cell compartments or cells. In addition, the introduced nucleic acid should be such that it can also be incorporated as replicative nucleic acid via cellular protein import routes. Properties should be present which result in a controlled transcription and/or replication in cells and in defined aimed (targeted) compartments of cell, respectively. The process is to be used for the therapy of genetic diseases (changes of the mitochondrial genome) and for the appropriate mutagenesis in eukaryotic and prokaryotic cells. The invention is to meet the following demands:

universal applicability cell-specific, compartment-specific and membrane-specific introduction behavior high degree of effectiveness low immunogenicity minimization of the infection risk the introduced nucleic acid (plasmid molecule) is to be replicatable the introduced nucleic acid (plasmic molecule) is to be transcribable the introduced nucleic acid (plasmid molecule) shall be resistant to nucleases the structure of the introduced nucleic acid (plasmid molecule) should be universally usable.

In order to be able to appropriately carry a protein within a cell from the site of formation to another compartment or another cell organelle (e.g. the site of action), the protein is usually synthesized as a preprotein (R. Zimmermann et al. (1983), "Biosynthesis and assembly of nuclear-coded mitochondrial membrane proteins in *Neurospora crassa*", Methods Enzymol. 97: 275–286). In addition to the Mature amino acid sequence, the preprotein has what is called a signal sequence. This signal sequence is specific to the aimed compartment and enables that the preprotein can be recognized by surface receptors. The natural obstacle 'membrane' is then overcome by translocating the preprotein through the membrane by an active (several 'transport proteins' are involved in this process) or passive process (direct passage without involvement of further proteins). Thereafter, the signal sequence is usually separated at the site of action by a specific peptidase unless it is a constituent of the matured mature protein. The mature protein can now provide its enzymatic activity.

The inventors have recognized that this mechanism can be utilized to appropriately transport nucleic acids across membranes. In this case, the nucleic acid is not subject to a restriction, i.e. it is possible to use every nucleic acid desired and known, respectively. For this purpose, a cell-specific, compartment-specific or membrane-specific signal sequence is linked with the desired nucleic acid, resulting in a chimeric peptide-nucleic acid fragment. In this context, it is known that the linkage between a nucleic acid and a peptide may occur via the α-amino group of a synthetic KDEL peptide, SEQ ID NO:16, modified by ε-maleimidocapronic acid-N-hydroxysuccinimide ester (K. Arar et al. (1993), "Synthesis of oligonucleotide-peptide conjugates containing a KDEL (SEQ ID NO:16) signal sequence", Tetrahedron Lett. 34: 8087–8090). However, this linkage strategy is completely unusable for the nucleic introduction into cell organelles and cells, since here the translocation should occur in analogy to the natural protein transport. Such a transport cannot be expected by blocking the α-amino group of a synthetic peptide by means of a nucleic acid. Therefore, the inventors chose linkage via a carboxy-terminal amino acid. On the one hand, this ensures a 'linear' linkage, on the other hand, the free amino-terminal end of the signal peptide is thus available for the essential steps of the import reaction.

In order to be able to utilize the described transport mechanism also for the introduction of replicative and transcription-active nucleic acids, the nucleic acid is preferably integrated via a homologous recombination into an existing genome or is itself the carrier of the genetic elements, which ensures an autonomous initiation of replication and transcription. Only the latter variant complies with the criterion of universal applicability, since a recombination into an existing cellular genome is successful only under certain conditions and in select cells.

In this case, the use of cyclic DNA represents one possibility, since the DNA polymerases at the end of the new synthesis of the daughter strands return to the initial point thus guaranteeing a complete DNA replication. Although the use of a double-stranded cyclic plasmid meets all physical criteria for a successful replication in every aimed compartment of the cell, this physical DNA form is confronted with the import pore size which is decisively involved in the appropriate translocation: Even the compact diameter of a superhelical plasmid can be compared with that of globular proteins, therefore, a translocation through a membrane system via the protein import route appears impossible. Here, an approach to a solution in involves the use of linear-cyclic DNA molecules having modified (cyclic) ends but only the diameter of linear DNA molecules. On the one hand, they are no obstacle for the import pore size; on the other hand, these linear-cyclic DNA molecules include all physical preconditions to be able to form replicative and transcription-active plasmids in the mitochondria.

The following is preferably required for the construction of the chimeric peptide-nucleic acid fragment according to the invention as well as for the construction of a replicative and transcription-active nucleic acid portion (plasmid):

signal peptide and signal sequence, respectively, (cell-specific, compartment-specific, or membrane-specific)

linkage agent nucleic acid (oligonucleotide) which may preferably comprise the following further information:

information on the initiation and regulation of transcription and replication, information as to the termination of transcription and replication multiple cloning site for a nucleic acid to be introduced (to be expressed) additionally, possible modifications, so that 'hairpin loops' can be added (cyclization of the ends) which permit linkage with the signal peptide.

The selection of the signal sequence depends on the membrane and membrane system, respectively, which is to be overcome and the aimed (targeted) compartment of the cell (cell nucleus, mitochondrion, chloroplast) or the cell organelle which is to be obtained. Proteins which are to be introduced e.g. into one of the four mitochondrial compartments (outer mitochondrial membrane, intermembraneous space, inner mitochondrial membrane, matrix space), have compartment-specific signal sequences. In general, signal sequences are chosen for the introduction of nucleic acids which contain a cell-specific, compartment-specific or membrane-specific recognition signal thus directing the attached nucleic acid to its site of action (e.g. inner side of the inner mitochondrial membrane or matrix space). A selection can be made among signal sequences which can transport proteins in the presence or absence of a membrane potential. For the nucleic acid introduction, signal sequences which function irrespective of the membrane potential are preferred, e.g. the signal sequence of ornithine transcarbamylase (OTC) for the transport into the matrix space of the mitochondria (A. L. Horwich et al. (1983), "Molecular cloning of the cDNA coding for rat ornithine transcarbamylase", Proc. Natl. Acad. Sci. U.S.A. 80: 4258–4262; J. P. Kraus et al. (1985), "A cDNA clone for the precursor of rat mitochondrial ornithine transcarbamylase: comparison of rat and human leader sequences and conservation of catalytic sites", Nucleic. Acids. Res. 13: 943–952). Basically, the pure signal sequence suffices for the transport into the aimed compartment. However, it is preferable to select signal sequences which additionally have a cell-specific or compartment-specific peptidase cleavage site. In the most favorable case, this 'cleavage site' is within the signal sequence but can also be attached thereto by additional amino acids to ensure the cleavage of the signal sequence when the aimed compartment has been reached (e.g. the signal sequence of human OTC can be by ten additional amino acids of the mature OTC). This ensures that the nucleic acid can be separated from the signal peptide in the aimed compartment, so that the action of the nucleic acid fully unfolds. The selected signal sequence is prepared biologically (purification of natural signal sequences or cloning and expression of the signal sequence in a eukaryotic or prokaryotic expression system) or preferably in a chemical-synthetic way.

In order to ensure a linear chemical linkage between nucleic acid and signal peptide, the signal peptide is linked via a linkage agent which is generally linked therewith via amino acids, preferably via amino acids having reactive side groups, preferably via an individual cysteine or lysine at the carboxy-terminal end of the signal peptide. A bifunctional cross-linker serves as a linkage reagent, preferably a heterobifunctional cross-linker which has a second reactive group, preferably an aminoreactive group, in addition to a thiol-reactive group at the signal peptide when a cysteine is used as the linkage site (e.g. m-maleinimidobenzoyl-N-hydroxy-succinimide ester, MBS and its derivatives).

The nucleic acid also has a linkage site which should be compatible with the selected cross-linker. When MBS is used, the oligonucleotide should have an amino function or thiol function. The linkage group of the nucleic acid can be introduced via the chemical synthesis of the oligonucleotide and is generally localized at the 5' end, at the 3' end, but preferably directly at a modified base, e.g. as 5' amino linker (TFA amino linker Amidite®, 1,6-(N-trifluoroacetylamino)-hexyl-β-cyanoethyl-N,N-diisopropyl phosphoramidite, Pharmacia) or a 5' thiol linker (THIOL-C6 Phosphoramidit®, MWG Biotech) at a free 5' hydroxy/phosphate group, as 3' amino linker (3' aminomodifier-C7-CPG-Synthesesäulen®, MWG Biotech) at a free 3' hydroxy/phosphate group, but preferably as amino-modified base analog, preferably amino-modified deoxyuridine (Amino-Modifier-dT®, 5'-dimethoxy-trityl-5[N-(trifluoroacetylaminohexyl)-3-acrylimido]-2'-deoxyuridine, 3'-[2-cyanoethyl)-(N,N-diisopropyl)] phosphoramidite, Glen Research) within the sequence. In this case, the reactive group compatible with the cross linker used is spaced from the 5' end or 3' end of the oligonucleotide or the modified base by at least one C2-spacer unit, but preferably by a C6-spacer unit. The nucleic acid (oligonucleotide) including a reactive linkage group then comprises at least two nucleotides.

In order to increase the stability of the nucleic acid (oligonucleotide) over cellular and extracellular nucleases, the chemically synthesized nucleic acids can be protected by a sulfurizing reagent (Beaucage-Reagenz®, MWG-Biotech). The phosphorus diester bonds of the nucleic acid are converted into phosphorus thioate bonds in the chemical synthesis. This oligonucleotide can then be used for the enzymatic amplification of nucleic acids, extended by further linkage reactions with other nucleic acids or used directly.

In order to directly use the chimeric peptide nucleic acid fragment, the nucleic acid (oligonucleotide) should have a secondary structure that can be hybridized, preferably without internal homologies so as to be able to form a linear single-strand structure. This ensures that the nucleic acid (oligonucleotide) of the chimeric peptide-nucleic acid fragment can provide a biochemical/therapeutic effect without further nucleic acid linkages.

However, for linkage with the signal sequence it is preferred to use nucleic acids (oligonucleotides) which have two further properties:

1. The sequence is preferably partially palindromic, has a blunt 5'–3' end ('blunt end'), an overhanging 3' end ('sticky end'), but has especially an overhanging, phosphorylated 5' end ('sticky end'), especially preferably an overhanging 5' end which comprises 4 nucleotides and has no self-homology (palindromic sequence). As a result, a stable, monomeric secondary structure ('hairpin loop') may form. The overhanging 5' end serves for linking defined nucleic acids, antisense oligonucleotides, but preferably transcribable and replicatable genes.

2. In the apex of the 'loop', the oligonucleotide carries a modified base which carries a grouping reactive with respect to the cross-linker, preferably an amino-modified 2'-deoxythymidine. In this case, the amino function of this modified base enables the linkage reaction between MBS and oligonucleotide.

The chimeric peptide-nucleic acid fragment is suitable for appropriately introducing nucleic acids into cells and cell organelles (e.g. nucleus, chloroplast), particularly for introducing ribonucleic acids (mRNA, 'antisense' oligonucleotides) and deoxyribonucleic acids (complete gene, 'antisense' oligonucleotides). It is especially suitable for the introduction of transcribable and processable genes into mitochondria, but even more suitable for the introduction of replicative, transcription-active and processable linear-cyclic nucleic acids (plasmids).

In a preferred embodiment, a transcribable gene is linked to the nucleic acid, containing the reactive linkage site, or to the chimeric peptide-nucleic acid fragment. This is effected preferably by the amplification of a gene, preferably a cloned gene consisting of a mitochondrial promoter, preferably the promoter of the light DNA strand ($0_L$, nt 490-nt 369) and the gene to be expressed in a processable form, preferably a mitochondrial gene, preferably a mitochondrial transfer RNA, preferably the mitochondrial tRNA$^{Leu(UUR)}$ (nt 3204-nt 3345) (S. Anderson et al. (1981), "Sequence and organization of the human mitochondrial genome", Nature 290: 457–465). Following the enzymatic amplification of the gene, the linkage to the nucleic acid, containing the reactive linkage site, or to the chimeric peptide-nucleic acid fragment can be effected via a 'blunt end' ligation, but preferably a 'sticky end' ligation. For this purpose, the nucleic acid to be linked has at least one end capable of linkage, which consists preferably of a 5' overhang which comprises 4 nucleotides and has no self-homology (palindromic sequence). If both ends are to be linked with 'hairpin loops', a nucleic acid will preferably be selected which has differing 5' overhangs which comprise 4 nucleotides and have no self-homology. It is especially preferred to use nucleic acids whose 5' ends also have no homology with respect to one another. For the modification of the ends (cyclization) it is then preferred to use two different 'hairpin loops', one being specific (complementary) to the 'left' plasmid end and the other being specific to the 'right' plasmid end of the nucleic acid. In order to increase the stability of the nucleic acid over cellular and extracellular nucleases, the phosphorus diester bonds of the nucleic acid can be substituted with phosphorus thioate bonds and thus be protected if modified phosphorus thioate nucleotides have been used already in the enzymatic amplification.

A process comprising the following steps is suitable for the production of a chimeric peptide-nucleic acid fragment:
(a) Reaction of a nucleic acid (oligonucleotide), containing a functional linkage group, with a linkage agent.
(b) Reaction of the construct resulting from (a) with amino acids at the carboxy-terminal end of a peptide, containing a signal sequence, with the exception of a KDEL (SEQ ID NO: 16) signal sequence, and (c) optional extension of the chimeric peptide-nucleic acid fragment resulting from (b) by further DNA or RNA fragments.

In another preferred embodiment, the chimeric peptide-nucleic acid fragment can be produced by the following steps:
(a) Optional extension of the nucleic acid, containing a functional linkage group, by further DNA or RNA fragments.
(b) Reaction of the nucleic acid with functional linkage group or the extended nucleic acid resulting from (a) with a linkage agent.
(c) Reaction of the construct resulting from (b) with amino acids at the carboxy-terminal end of a peptide, containing a signal sequence, with the exception of a KDEL (SEQ ID NO: 16) sequence.

In another embodiment which is a linear-cyclic nucleic acid in the form of a plasmid, the selection of the nucleic acid depends on the genetic information which shall be expressed in which cell and in which aimed compartment of the cell. In this connection, nucleic acids which are to be transcribed have to have a suitable promoter. For example, if a gene is to be expressed in the mitochondrial matrix, a mitochondrial promoter can be chosen, preferably the promoter of the to light mtDNA strand. The transcription is controlled in other cell compartments (e.g. nucleus, chloroplast) by compartment-specific promoters.

The transcription is usually regulated by what is called transcription regulation sequences, preferably mitochondrial transcription regulation sequences. In general, these sequences comprise at least binding sites for factors which initiate the transcription (transcription initiation factor) as well as the binding site for the RNA synthesis apparatus. If a transcription is to be initiated in the mitochondria, binding sequences of the mitochondrial transcription factors and of the RNA polymerase, particularly of the mitochondrial transcription factor 1 and the mitochondrial RNA polymerase, will be suitable. In other cell compartments (e.g. nucleus, chloroplast), the transcription can be controlled by compartment-specific transcription-regulation sequences.

In order to be able to regulate the transcription, the plasmid has transcription regulation sequences which are attached preferably in the 3' direction of the transcription initiation site (promoter). For example, if the transcription of a mitochondrial transformation plasmid is to be regulated, the control elements will be suitable for the H-strand and L-strand transcription of the mitochondrial genome, however preferable would be the so-called 'conserved sequence blocks' which terminate the transcription of the L-strand and simultaneously enable the transition to DNA replication. In order to induce the exclusive transcription of the desired gene (optionally the desired genes in a polycistronic transcription), the transcription is discontinued on a suitable site behind the 3' end of the expressible gene/genes. This is achieved by the insertion of a suitable transcription-termination site, preferably arranged in the 3' direction to the promoter. For the regulated expression, the binding sequence for a bidirectionally acting transcription-termination factor is especially suitable in this case. For the transcription-termination in the mitochondria, a binding motif of a mitochondrial transcription-termination factor is preferably chosen here. At the same time, the formation of 'antisense RNA' of the head-to-head-linked dimeric plasmids is suppressed by the use of the transcription-termination factor binding sequence.

The selection of transformed cells can be controlled via the expression of a reporter gene. Genes whose expression result in a macroscopic change of the phenotype are especially suitable as reporter or selection genes. A selection is made among genes which produce resistances to antibiotics, for example. In particular, the resistance genes for oligomycin (OLI) or chloramphenicol (CAP) are suitable for the use in a mitochondrial transformation system. In this connection, the mitochondrial chloramphenicol resistance gene appears to be a particularly suitable selection gene, since CAP-sensitive cell lines already change their phenotype at a portion of about 10% of the 16 S rRNA$^{CAP+}$ gene.

The replication of the nucleic acid can be realized by an initiation site for the DNA replication (replication origin). Therefore, the chimeric peptide-nucleic acid fragment in the form of a plasmid has to have at least one replication origin. In this connection, the orientation of the replication origin can be arranged irrespective of the expressible gene (genes), but preferably the replication origin is arranged in the 3' direction of the promoter. A suitable replication origin for a mitochondrial transformation plasmid would be a mitochondrial replication origin. In particular, the origin of replication of the heavy mtDNA strand is suitable in this case. It preferably has at least one 'conserved sequence block'. The replication can be controlled via what is called regulation sequences for the replication. For this purpose, the plasmid has to have at least one such sequence motif which is preferably arranged in the 3' direction of the promoter and the replication origin. If the replication in the mitochondria is to be regulated, a mitochondrial replication regulation sequence will be especially suitable. It is preferred to use a motif which comprises at least one of the 'termination associated sequences'. In other cell compartments (e.g. nucleus, chloroplast), the replication is initiated at least via one compartment-specific replication origin and controlled via compartment-specific replication regulation sequences.

In order to permit cloning of different genes into the plasmid molecule, the plasmid nucleic acid also has to have a suitable cloning module (multiple cloning site) which has the most widely differing recognition sequences for restriction endonucleases. Here, rare recognition sequences which do not occur at other sites of the plasmid are especially suitable. The cloning module can be incorporated into any site of the transformation plasmid. If the region of the cloning site is to be integrated into the transcription of the selection gene, the insertion of the multiple cloning site in the 3' direction of the promoter and in the 5' direction of the transcription termination site will be suitable. The integration of the multiple cloning site in the 5' direction of the selection gene is especially suitable, since in this case the use of the selection system is simultaneously accompanied by a transcription of the region of the multiple cloning site.

In order to permit the autonomous replication in every aimed compartment of a cell when a nucleic acid is used, it has to be ensured that, after the synthesis of the daughter strand, the DNA replication enzymes return to the synthesis starting point again to guarantee the covalent linkage of the 3' end with the 5' end of the newly synthesized daughter strand by corresponding enzymes. For this purpose, a linear nucleic acid plasmid is suitable which can be converted into a cyclic nucleic acid. The plasmid ends can be cyclized via the use of what is called ligation-capable (phosphorylated) ends of nucleic acid. For this purpose, the use of a 'blunt end' nucleic acid or a nucleic acid having a overhanging 3' ends, but preferably a nucleic acid having overhanging 5' ends is particularly suitable. In this case, the overhanging ends should comprise at least one nucleotide. However, it is preferred to use overhanging 5' ends which are formed of four nucleotides. They have preferably no self-homology (palindromic sequence) and are also preferably not complementary to one another in order to suppress the formation of dimers in a subsequent nucleic acid linkage.

The cyclization of the prepared plasmid ends is arranged by synthetic oligonucleotides. They have a partial self-homology (partially palindromic sequence) and are thus capable to can form what is called 'hairpin loop' structures. The partially palindromic sequence results in the formation of a stable, preferably monomeric secondary structure ('hairpin loop') having a blunt 5'–3' end (blunt end), an overhanging 3' end ('sticky end'), but preferably an overhanging 5' end. These oligonucleotides are especially preferred when they have a phosphorylated 5' end. When synthetic oligonucleotides having 'hairpin loop' structure are used, the linear plasmid DNA can be converted into a linear-cyclic system. The ends of the two oligonucleotides are each preferably complementary to one end of the prepared plasmid nucleic acid. For this purpose, two different 'hairpin loops' are preferably used, one being specific (complementary) to the 'left' plasmid end, one being specific (complementary) to the 'right' plasmid end to suppress dimer formation. At least one of the two 'hairpin loop' oligonucleotides may have at least one modified nucleotide. It guarantees the linkage site to a signal peptide, so that the nucleic acid transport can be arranged via the protein import route. In the model case, this linkage site (modified nucleotide) is placed at one of the unpaired positions of the 'loop'. A chemically reactive group, particularly an amino or thiol function, is especially suitable as linkage site.

In order to prepare the ends of the transformation plasmid for the modification (cyclization), it has to be ensured that the plasmid ends are complementary to the ends of the oligonucleotides ('hairpin loops'). On the one hand, this succeeds by amplifying the plasmid DNA with suitable oligonucleotides which have at least one recognition sequence for a restriction endonuclease. In this case, recognition sequences for restriction endonucleases are suitable which do not occur repeatedly in the plasmid sequence. Especially suitable is the use of recognition sequences for restriction endonucleases generating overhanging ends ('sticky ends'), particularly those which produce overhanging 5' ends, preferably outside the recognition sequence. In this connection, the recognition sequence for the restriction endonuclease Bsa I ($GGTCTCN_1N_5$) is especially suitable. On the other hand, the use of a cloned nucleic acid which already has the recognition sequences for a restriction endonuclease, preferably Bsa I, is suitable. As a result, the enzymatic amplification can be omitted and the nucleic acid obtained by plasmid preparation/restriction enzyme treatment can be used directly. It is preferred that the cloned nucleic acid already includes the recognition sequence for the restriction endonuclease Bsa I at both ends.

Various methods are available for purifying the transformation plasmid. Here, the main objective is to separate the cyclic plasmid molecule from the unreacted adducts. The use of DNA-degrading enzymes are proved to be suitable in this connection. In particular, it is recommended to use enzymes which have a 5'–3' or 3'–5' exonuclease activity. Particularly the use of the exonuclease III leads to the complete hydrolysis of unreacted adducts while the cyclic plasmid DNA remains intact (no free 5' ends or 3' ends). The reaction products can be purified either via electrophoretic or chromatographic processes but also by precipitation. A selection can be made among different purification processes. On the one hand, the cyclic nucleic acid conjugated with the linkage agent and the signal peptide can be treated with an exonuclease, preferably exonuclease III, and then be purified via chromatographic, electrophoretic purification and precipitation, respectively. On the other hand, the cyclic plasmid DNA can also be treated with an exonuclease, preferably exonuclease III, be purified and subsequently be conjugated with the linkage agent and the signal peptide and be purified via a chromatographic, electrophoretic purification and precipitation, respectively.

The linkage with a signal peptide can be realized by means of modified oligonucleotides. This peptide directs in vivo the transformation plasmid into the desired cell compartment. To this end, either the transformation plasmid can first be reacted with the modified oligonucleotide (ligation) and then the conjugation with the linkage agent and the signal peptide can take place or the modified oligonucleotide is first conjugated with the linkage agent and the signal peptide and can then be used for cyclizing the transformation plasmid ends (ligation).

The transformation system (cellular transformation) can penetrate the cell membrane by various methods. Here, the 'particle gun' system or microinjection are suitable, but electroporation and lipotransfection are preferred. All methods ensure the introduction of the linear-cyclic peptide nucleic acid plasmid into the cytosol of the cell from where the plasmid is directed to its site of action (aimed compartment) by the conjugated signal peptide.

As compared to the prior art transformation and infection methods, mentioned in the introductory part of the description, this process offers, for the first time, the possibility of appropriately introducing nucleic acids into cells and cell organelles. The selection of the signal sequence can determine the aimed compartment which is to be reached in this case (cytosol, nucleus, mitochondrion, chloroplast, etc.). Along with the compartment-specific and cell-specific introduction behavior, this process distinguishes itself by its universal applicability. Both prokaryotic and eukaryotic cells and cell systems can be treated with the translocation vector. Since a natural transport system of the membranes is used for the appropriate introduction, the treatment of the cells or cell organelles with membrane-permeabilizing agents becomes superfluous (e.g. calcium chloride method, see above).

When a replicative and transcription-active nucleic acid is used, the plasmid does not unfold its full size until the first replication cycle has been completed: As a genuine cyclic plasmid (artificial chromosome) it now has the double genetic information (head-to-head linked plasmid dimers). In particular with respect to the use of this system for a somatic gene therapy, this behaviour is induced intentionally and of decisive importance, since the genes to be expressed have to compete with the defective genes of the cells. In addition to this highest possible effectiveness, the system distinguishes itself through the fact that it does not have to be integrated into a genome via a recombination step, such as retroviral systems, so as to become replicative. As a result, uncontrollable side-effects (undesired recombination) are already suppressed to the highest possible degree from the start. Therefore, the application of this plasmid system can be expected without great safety risk.

The present invention is now explained by way of the below examples which, however, shall not at all restrict the invention.

EXAMPLES

Example 1

Figure 1:
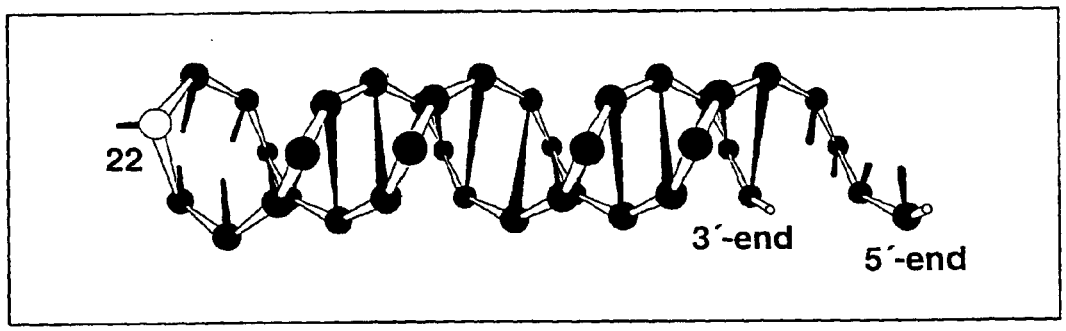
FIG. 1 shows a signal peptide of the ornithine transcarbamylase of rats as well as a DNA sequence suitable for the introduction. Top: signal peptide of the ornithine transcarbamylase of rats (32 amino acids, SEQ ID NO:1), extended by 10 N-terminal amino acids of the matured protein and an additional cysteine as linkage site. The peptide sequence is shown in the international one-letter code; middle: a partially palindromic DNA sequence suitable for the introduction and consisting of 39 nucleotides having an amino-modified T at nucleotide position 22; bottom: marked secondary structure of the oligonucleotide having an overhanging 5' end and a modified nucleotide in the vertex of the 'loop'. See also SEQ ID NO:22.
Figure 2:
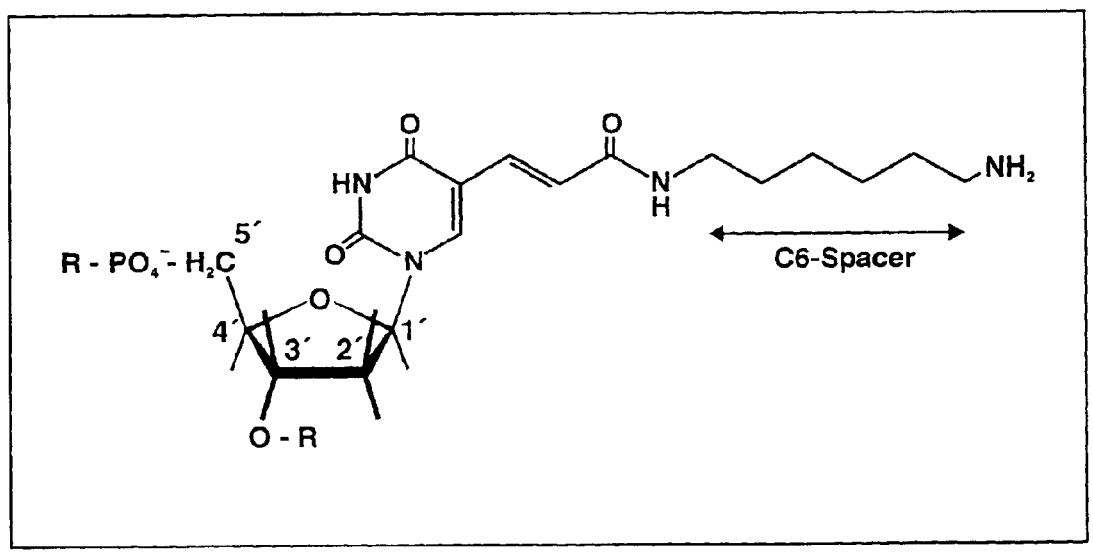
FIG. 2 shows the structure of the amino-modified 2'-deoxythymidine, R: nucleic acid residues.

Introduction of a chimeric peptide-nucleic acid fragment into the mitochondria The overcoming of the mitochondrial double membrane system with a DNA translocation vector was studied to prove that nucleic acids can be transported appropriately across membranes by the above-described process. For this purpose, the mitochondrial signal sequence of the ornithine transcarbamylase (A. L. Horwich et al. (1983), "Molecular cloning of the cDNA coding for rat ornithine transcarbamylase", Proc. Natl. Aca. Sci. U.S.A. 80: 4258–4262) (enzyme of urea cycle, naturally localized in the matrix of the mitochondria) was chemically prepared and purified. The original sequence was extended by a cysteine at the C terminus as reactive group for the subsequent linkage with the DNA (see FIG. 1 and SEQ ID NO:1). This ensured that the heterobifunctional cross-linker (MBS) can only be linked with the thiol group of the only cysteine. A DNA oligonucleotide (39 nucleotides) were chosen as linkage partner. It distinguishes itself by two special features:

1. The sequence is partially palindromic and has an overhanging, phosphorylated 5' end (see SEQ ID NO:1 and FIG. 1). As a result, what is called a 'hairpin loop' can form. The overhanging 5' end serves for ligating to this oligonucleotide defined nucleic acids which can then be imported into the mitochondria.
2. The oligonucleotide carries a modified base in the vertex of the 'loop' (see FIG. 1). In this case, an amino-modified 2'-deoxythymidine is concerned (see FIG. 1). Here, the amino function of the modified bases in this connection enables the linkage reaction between MBS and oligonucleotide.

Figure 3:
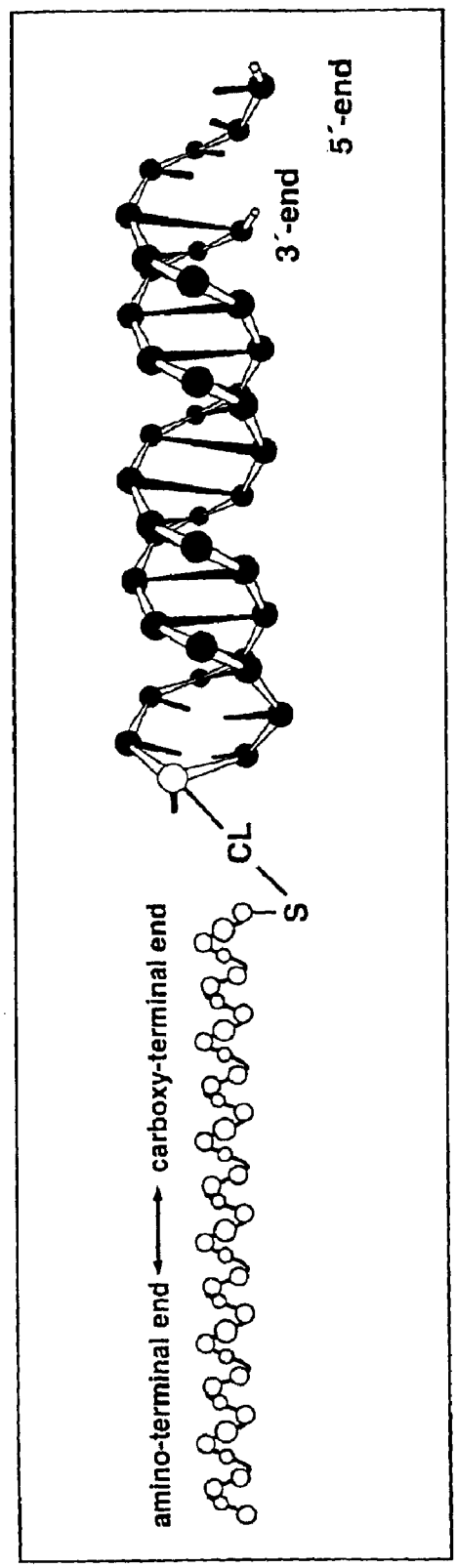
FIG. 3 shows a diagram of the chimeric peptide-nucleic acid fragment, consisting of amino-modified oligonucleotide (39 nucleotides) with marked 'hairpin loop', cross-linker and signal peptide. CL: cross-linker.
Figure 4:
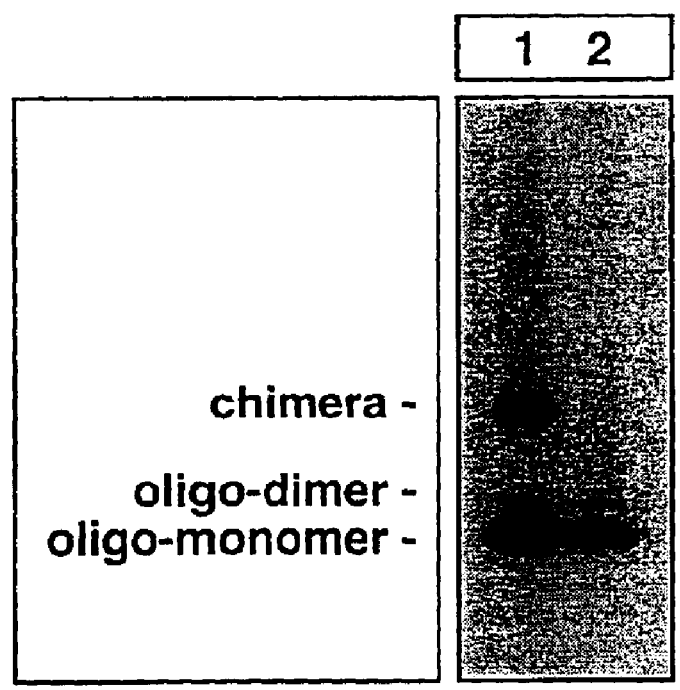
FIG. 4 shows the electrophoretic separation of the linkage product resulting from amino-modified oligonucleotide (39 nucleotides), m-maleimidobenzoyl-N-hydroxy-succinimide ester (MBS) and signal peptide of the ornithine transcarbamylase of rats (42 amino acids, extended by a cysteine at the C terminus).

The three reaction partners (oligonucleotide, MBS and peptide) are linked in individual reaction steps. Firstly, the oligonucleotide (50 pmoles) is reacted in a buffer (100 μg; 50 mM potassium phosphate, pH 7.6) with MBS (10 nmoles dissolved in DMSO) (reaction time: 60 min.; reaction temperature: 20° C.). Unreacted MBS is separated via a Nick-spin column® (Sephadex G 50, Pharmacia) which was equilibrated with 50 mM of potassium phosphate (pH 6.0). The eluate contains the desired reaction product and is reacted in another reaction step with the peptide (2.5 nmoles) (reaction time: 60 min.; reaction temperature 20° C.). The reaction was stopped by the addition of dithiothreitol (2 mM). The linkage product (chimera, see FIG. 3) was separated via preparative gel electrophoresis of unreacted educts adducts and isolated from the gel by electroelution (see FIG. 4). Differing nucleic acids can now be linked by simple ligation to the overhanging 5' end of the oligonucleotide.

Figure 5A:
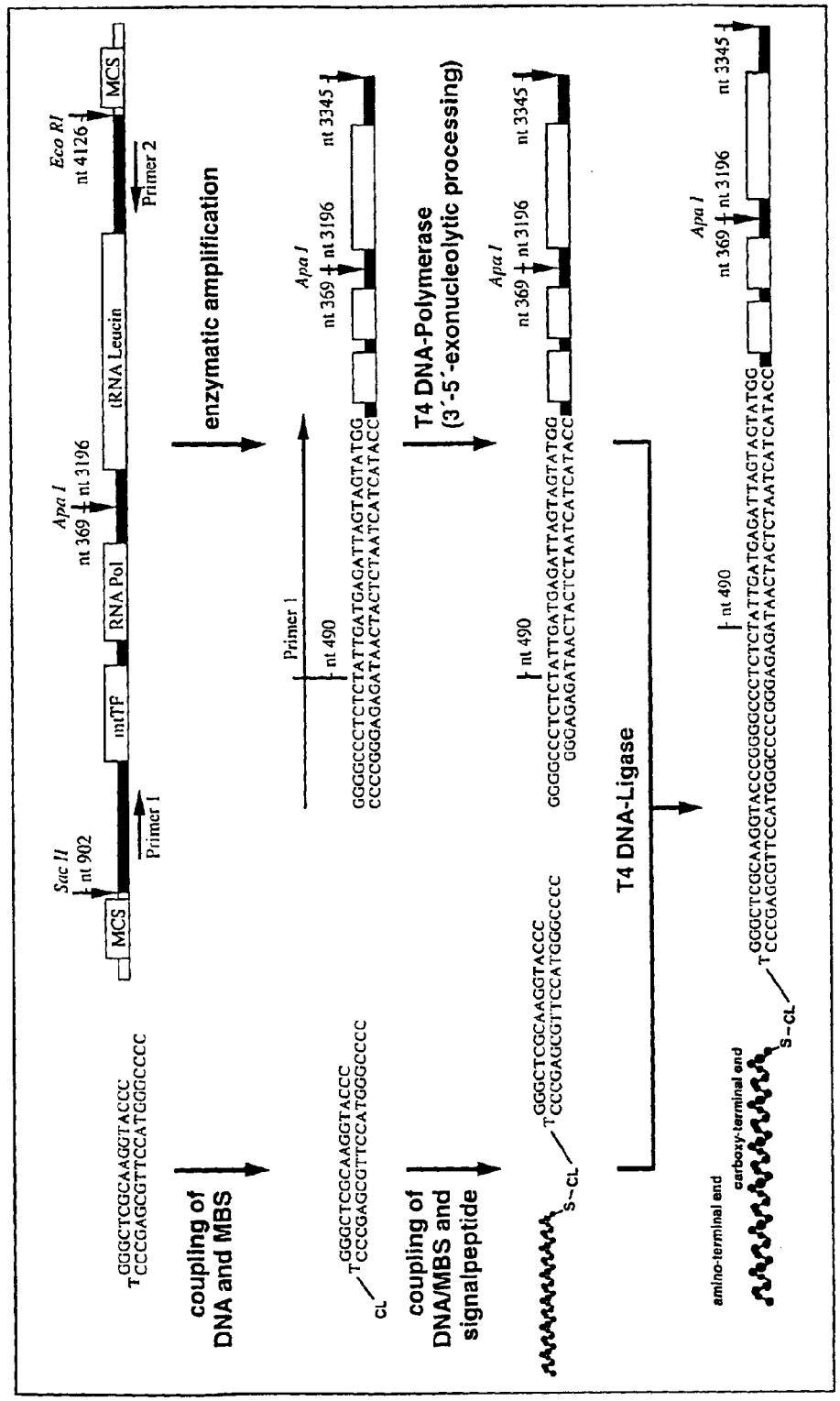
FIG. 5a shows a flow diagram of the peptide-DNA fusion, cloning, amplification and linkage of the transcribable and processable mitochondrial tRNA gene to be introduced (S. Anderson et al. (1981), "Sequence and organization of the human mitochondrial genome", Nature 290: 457–465). See SEQ ID NOs:2–6. CL: cross-linker (MES); MCS: multiple cloning site of pBluescrip® (Stratagene), mtTF: binding site of the mitochondrial transcription factor; RNA-Pol: binding site of the mitochondrial RNA polymerase; tRNA Leucine: gene of the mitochondrial transfer RNA for leucine (UUU); Sac II, APA I, Eco RI: sites for restriction endonucleases; the cloned mitochondrial sequences were numbered in accordance with the published sequence of the human mitochondrial genome (S. Anderson et al. (1981), "Sequence and organization of the human mitochondrial genome", Nature 290: 457–465).

A 283 bp long double-stranded DNA (dsDNA) was amplified via an enzymatic reaction (PCR) in the below experiment. For this purpose, a DNA fragment cloned into pBluescriptR (Stratagene) served as template DNA, which fragment in addition to the human mitochondrial promoter of the light strand ($P_L$, nt 902–nt 369) included the gene for the mitochondrial transfer RNA leucine (tRNA$^{Leuc\ (UUR)}$), nt 3204–nt 4126) (see FIG. 5). Two oligonucleotides served as amplification primers, primer 1 (SEQ ID NO: 17) having a non-complementary 5' end (see FIG. 5). The dsDNA was modified by the 3'–5' exonuclease activity of the T4 DNA polymerase (incubation in the presence of 1 mM dGTP) which can produce overhanging 5' ends under conditions with which a person skilled in the art is familiar (C. Aslanidis et al. (1990), "Ligation-independent cloning of PCR products (LIC-PCR)", Nucleic. Acids. 18: 6069–6074).

Together with the previously conjugated peptide-MBS oligonucleotide the PCR-amplified DNA could be joined using the T4 DNA ligase. In order to be able to easily detect the linkage partners after the introduction into the mitochondria, the free 5'-OH group of the ligated DNA was phosphorylated radioactively by an enzymatic reaction (A. Novogrodsky et al. (1966), "The enzymatic phosphorylation of ribonucleic acid and deoxyribonucleic acid, I. Phosphorylation at 5'-hydroxyl termini", J. Biol. Chem. 241: 2923–2932; A. Novogrodsky et al. (1966), "The enzymatic phosphorylation of ribonucleic acid and deoxyribonucleic acid. II. Further properties of the 5'-hydroxyl polynucleotide kinase", J. Biol. Chem. 241: 2933–2943).

Figure 6A:
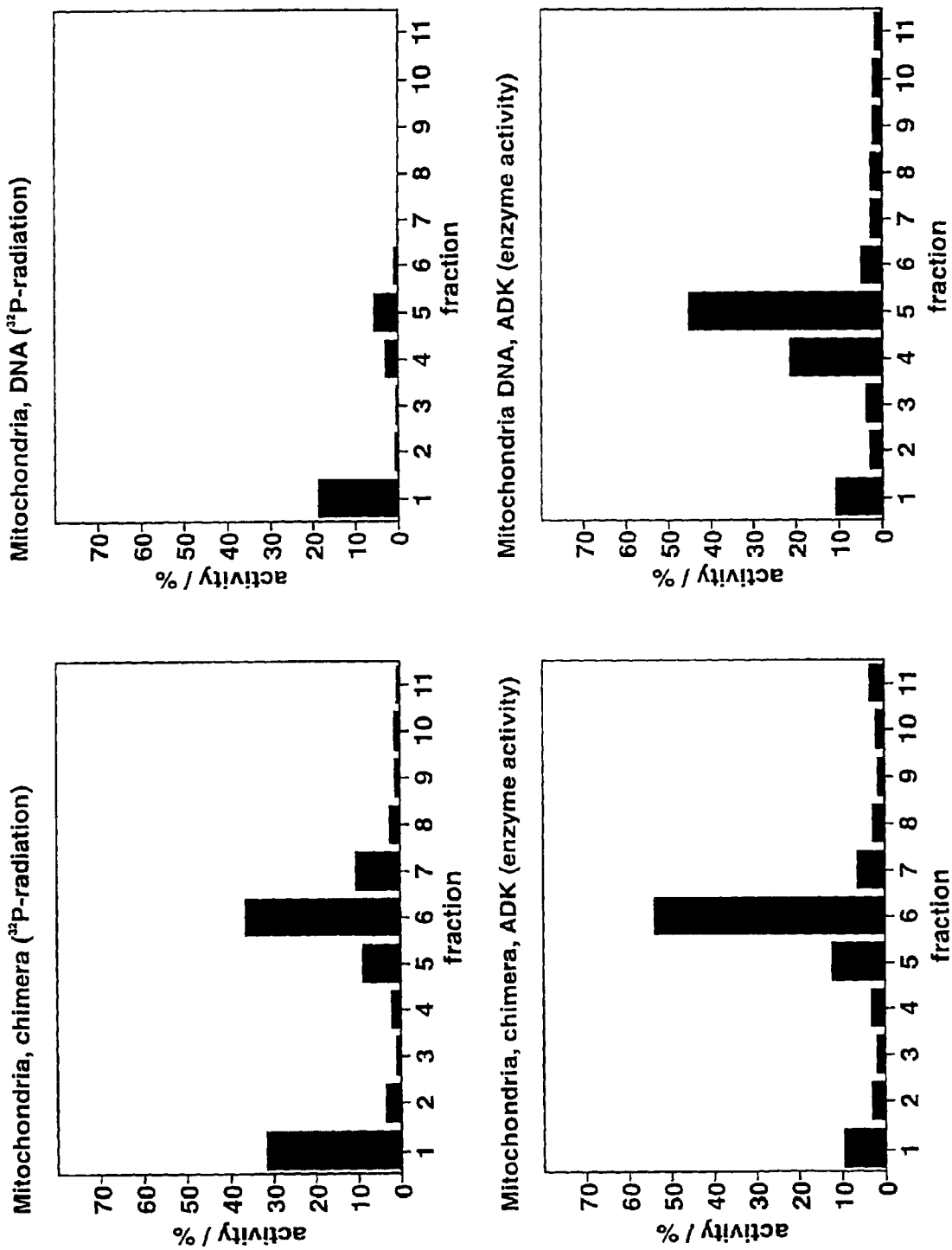
Figure 7A:
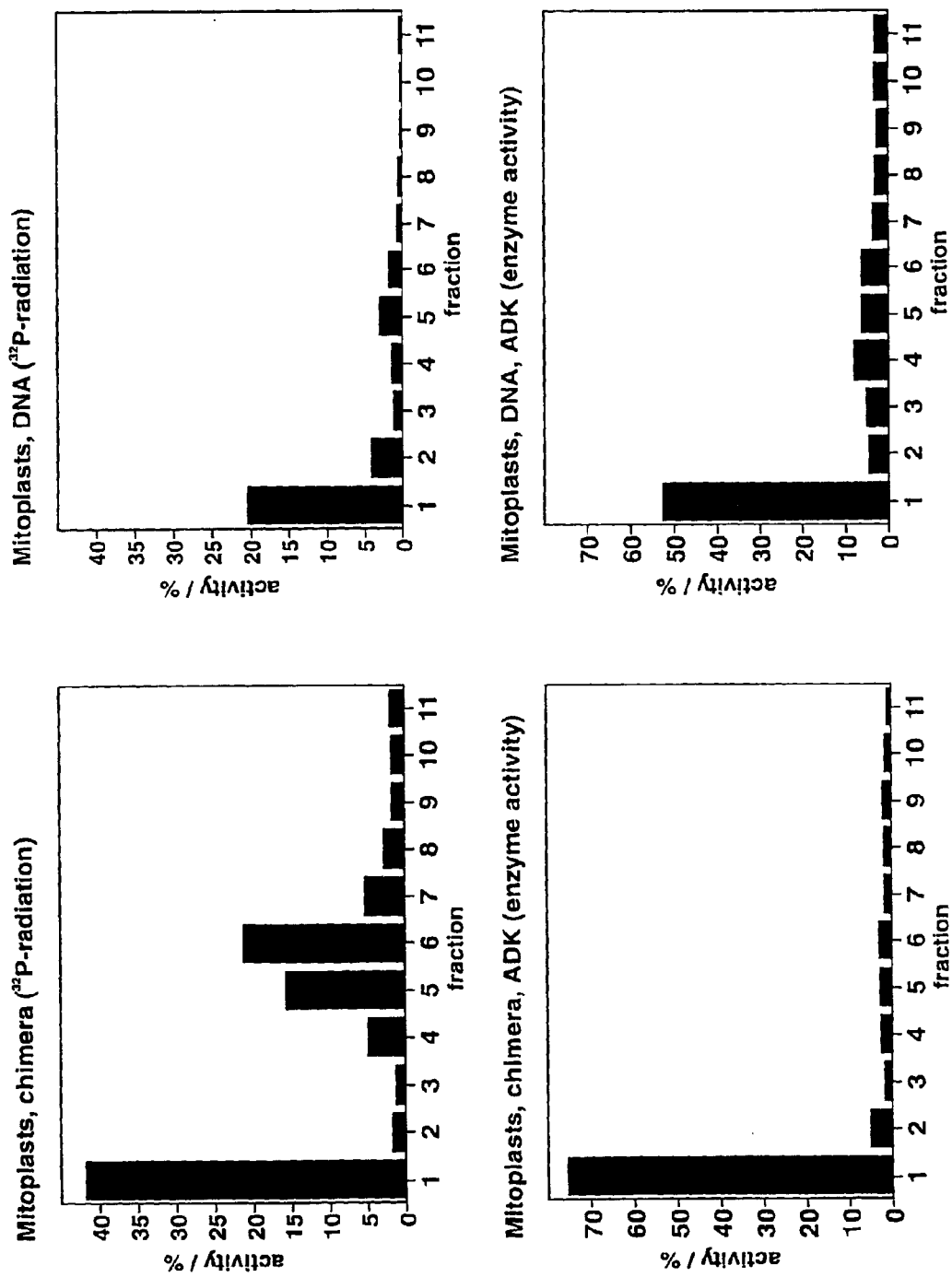
FIGS. 7a and 7b show the distribution of radioactivity, ADK, COX and MDH activities after introduction of DNA with and without the mitochondria-specific signed peptide after mitoplast sucrose density gradient centrifugation. The particular percentage of the total radioactivity/enzyme activity which was plotted against the gradient fraction number is illustrated. ADK: adenylate kinase; COX: cytochrome c oxidase; MDH: malate dehydrogenase.
Figure 7B:
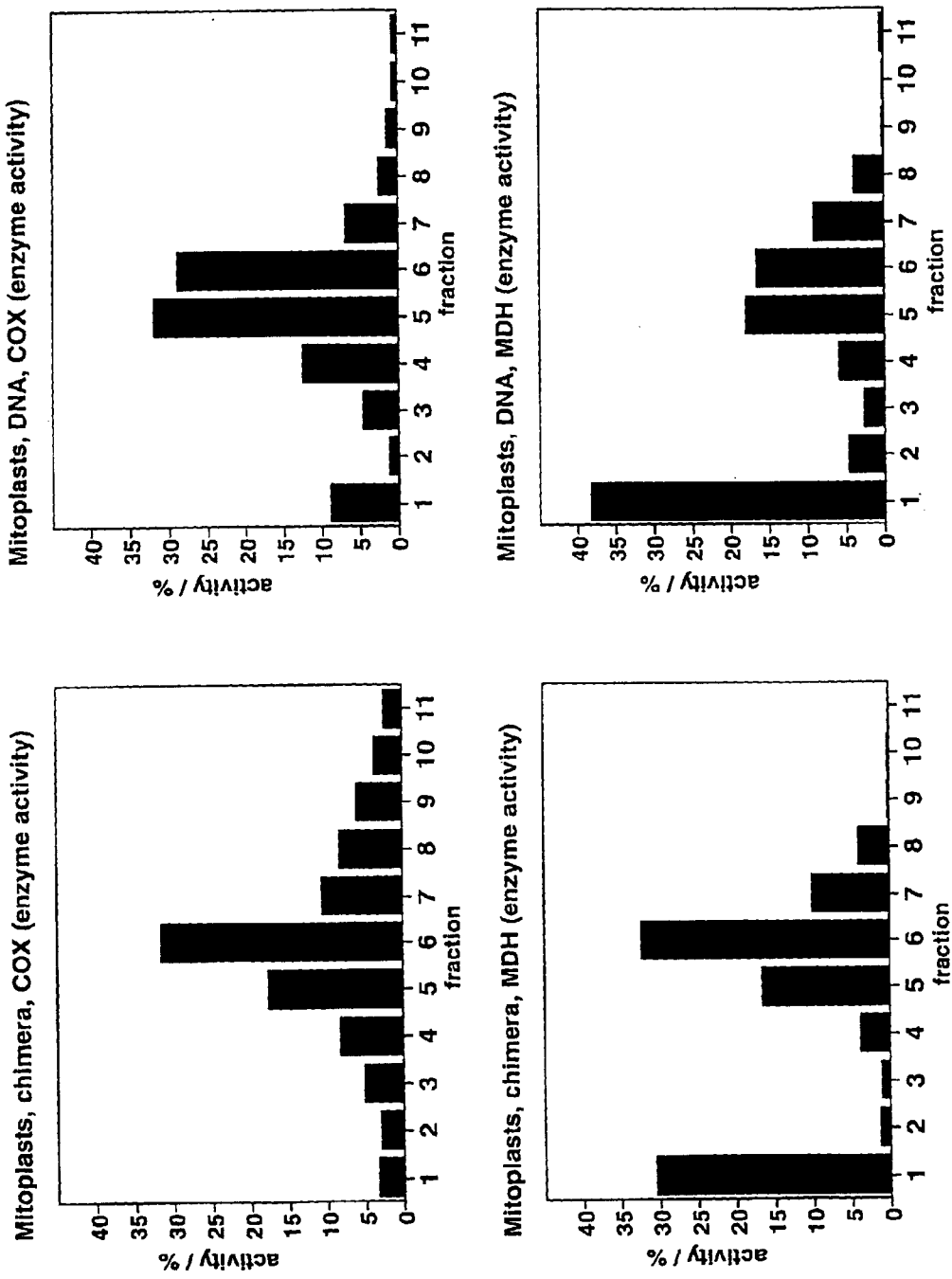

A fresh rat liver was comminuted for the isolation of mitochondria, suspended in 25 mM HEPES, 250 mM saccharose, 2 mM EDTA, 52 μM BSA and homogenized in a glass homogenizer (50 ml). Cell membranes, cellular debris and nuclei were centrifuged off at 3000 g and the supernatant was prepared for another centrifugation. For this purpose, the supernatant was placed in cooled centrifuge cups and centrifuged at 8000 g. The isolated mitochondria were resuspended in 200 ml of the same buffer and centrifuged again at 8000 g. The purified mitochondria pellet was resuspended in an equal volume of the same buffer and energized by the addition of 25 mM succinate, 25 mM pyruvate and 15 mM malate. The protein content of the suspension was determined by a Bradford Testkit® (Pierce). 2001 μg of mitochondrial protein (energized mitochondria) were incubated together with 10 pmoles of the chimera at 37° C. for 60 min. (0.6 M sorbitol, 10 mM potassium phosphate pH 7.4, 1 mM ATP, 2 mM $MgCl_2$, 1% BSA). The mitochondria were reisolated by centrifugation at 8000 g, resuspended in 0.6 M sorbitol, 10 mM potassium phosphate pH 7.4, 2 mM $MgCl_2$, 1% BSA, 10 U/ml DNAse I and incubated at 37° C. for 30 min. This washing step was repeated twice to remove non-specifically adhering molecules. For proving that the chimera is associated with the mitochondria, the re-isolated mitochondria were purified via sucrose gradient density centrifugation. The individual fractions of the gradient were analyzed to localize the chimera and the mitochondria. The adenylate kinase which determines cytochrome-c oxidase and malate dehydrogenase activity was used as marker for the mitochondria, while the chimera could be identified via the $^{32}P$ radioactivity measurement (see FIG. 6a). An analogous experiment for determining the non-specific DNA introduction was carried out with the same DNA which was not linked with the signal peptide (see FIGS. 6a–6b). It was derived from the measurements that 65% of the chimera used segregated specifically with the mitochondria, whereas the non-specific DNA incorporation was less than 5% of the DNA used. In order to show that the chimera is not only associated with the surface of the mitochondria (membrane, import receptor), the re-isolated mitochondria were not fractioned into the three compartments of outer mitochondria membrane/intermembranous space, inner mitochondrial membrane and matrix space. For this purpose, the mitochondria were incubated with digitonin (final concentration: 1.2% w/v digitonin) and the resulting mitoplasts were separated via a sucrose gradient density centrifugation, collected in fractions and the activities of marker enzymes (adenylate kinase: intermembranous space, cytochrome c oxidase: inner mitochondrial membrane; malate dehydrogenase: matrix space) were determined according to Schnaitman and Grennawalt (C. Schnaitman et al. (1968), "Enzymatic properties of the inner and outer membranes of rat liver mitochondria", J. Cell Biol. 38: 158–175; C. Schnaitman et al. (1967), "The submitochondrial localization of monoamine oxidase. An enzymatic marker for the outer membrane of rat liver mitochondria", J. Cell Biol. 32: 719–735) (see FIGS. 7a–7b). An analogous experiment for determining the non-specific DNA incorporation was carried out with the same DNA which was not linked with the signal peptide (see FIGS. 7a–7b). It was derived from the measurements that 45% of the chimera are associated with the mitoplasts, whereas the non-specifically adhering DNA could be assessed to be less than 3%. The isolated mitoplasts (loss of the outer membrane and the intermembranous space) were lysed by Lubrol® (0.16 mg/mg protein; ICN) and separated into the compartments of inner mitochondrial membrane (pellet) and matrix space (supernatant) by ultracentrifugation at 144,000 g. The compartments were assigned via the measurement of the activities of the cytochrome c oxidase (inner mitochondrial membrane) and the malate dehydrogenase (matrix space). The chimera was measured via the detection of the $^{32}P$ radioactivity in the scintillation counter and the result was 75% segregation with the matrix of the mitochondria, while 25' of the chimera remained associated with the inner membrane of the mitochondria (incomplete translocation).

Example 2

Incorporation of a Replicative and Transcription-Active Chimeric Peptide-Nucleic Acid Fragment (Plasmid) into the Mitochondria of Living Cells In order to prove that a linear peptide-nucleic acid plasmid having cyclic ends ('hairpin loops') can pass through membranes in vivo via the protein import route and can be transcribed and replicated in spite of the chemical linkage with a signal peptide, the transcription and replication behavior were studied after the transfection of cells and the import into the matrix of the mitochondria. For this purpose, the signal peptide of the mitochondrial ornithine transcarbamylase was prepared synthetically, purified and linked with a nucleic acid plasmid.

Figure 8:
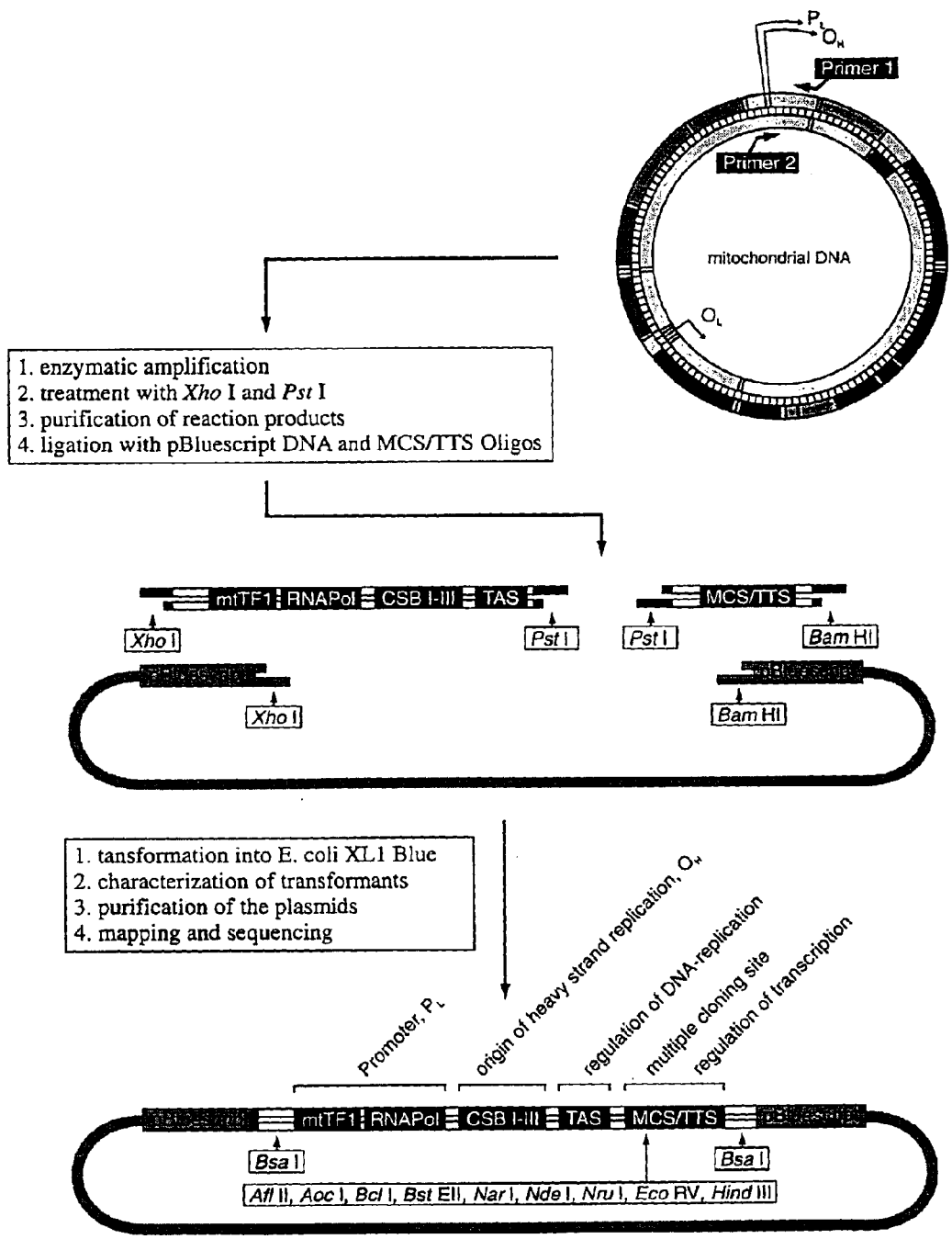
FIG. 8 shows the cloning of the nucleic acid portion of the peptide-nucleic acid plasmid into pBluescript (plasmid 1). Using the two oligonucleotides (primers 1 and 2), the gene section of nucleotide 15903 to nucleotide 677 was amplified enzymatically from mitochondrial HeLa DNA (comprises.

A precondition for the examination of the correct transcription and replication behavior is the physical structure of the plasmid: for the experiment described below, a 3232 bp long double-stranded vector DNA (dsDNA) was cloned into pBluescript® (Stratagene). For this purpose, the region of the mitochondrial genome was amplified via two modified oligonucleotides (primer 1, SEQ ID NO: 17, hybridized with the nucleotides 15903–15924 of the human mtDNA, includes at the 5' end an extension by the sequence TGTAGctgcag for the incorporation of a Pst I site; primer 2, SEQ ID NO:18, hybridized with the nucleotides 677–657 of the human mtDNA, includes at the 5' end an extension by the sequence TTGCATGctcgagGGTCTCAGGG for the incorporation of an Xho I site, which comprised the promoter of the light DNA strand, the origin of the mtDNA replication of the heavy strand, the regulation motifs for the transcription (CSBs, 'conserved sequence blocks') as well as the regulation site for the DNA replication ('TAS', termination associated sequences, (D. C. Wallace (1989), "Report of the committee on human mitochondrial DNA", Cytogenet. Cell Genet. 51: 612–621) (see FIG. 8). A multiple cloning site was inserted behind this fragment (3' direction), which is to permit an easy linkage with a gene to be expressed. The multiple cloning site (MCS/TTS) was produced via a chemical synthesis of two complementary oligonucleotides (MCS/TTS 1 and 2) which contain the recognition sequences for various restriction endonucleases (see FIG. 9). Under conditions with which a person skilled in the art is familiar, the two oligonucleotides form hybrids which, after the phosphorylation with T4 DNA polynucleotide kinase, can be used for the ligation. In this connection, the hybrids distinguish themselves by 5' and 3' single-stranded-overhanging ends which are complementary to a Pst I, on the one hand, and are complementary to a Bam HI site, on the other hand (see FIG. 9). Together with the multiple cloning site, the synthetic oligonucleotides MCS/TTS 1 and 2 also comprise a bidirectional mitochondrial transcription termination sequence (see FIG. 9). It is arranged in the 3' direction of the MCS and ensures that the transcription on this site is discontinued, thus correctly forming terminated transcripts. This sequence motif also ensures that in the cyclic plasmid system no 'antisense RNA' is expressed. The ligation reaction between pBluescript, PCR-amplified fragment and the MCS/TTS hybrids took place in a stoichiometry of 1:2:2 under conditions with which a person skilled in the art is familiar. After the transformation, several E. coli colonies (clones) could be isolated and characterized. For this purpose, the corresponding plasmid DNA was subjected to dideoxy sequencing (FIG. 10) under conditions with which a person skilled in the art is familiar.

For the experimental examination of the replication and transcription, what is called a reporter gene was inserted in the multiple cloning site. The chloramphenicol-resistant human mitochondrial 16 S ribosomal RNA was chosen as the reporter gene. It distinguishes itself from the naturally occurring ribosomal RNA only by a modified nucleotide (polymorphism). By means of the polymerase chain reaction, a fragment having two modified oligonucleotides (primer 3, SEQ ID NO: 19, hybridized with the nucleotides 1562–1581 of the mitochondrial DNA, extended at the 5' end by the sequence CCTCTaagett for the incorporation of a Hind III site; primer 4, SEQ ID NO:20, hybridized with the nucleotides 3359–3340, extended at the 5' end by the sequence GCATTactagt for the incorporation of a Bcl I site) was amplified from a DNA extract of chloramphenicol-resistant HeLa cells under conditions with which a person skilled in the art is familiar. In order to ensure a correct processing of the subsequent transcript, the amplification product included the two flanking tRNA genes (tRNA$^{Val}$ and tRNA$^{Leu}$). The amplified DNA was treated with the restriction endonucleases Hind III and Bcl I, purified by precipitation and used with the pBluescript plasmid 1 treated with Hind III and Bcl I (see FIGS. 8, 9 and 10) in a stoichiometry of 1:1 in a ligation reaction under conditions with which a person skilled in the art is familiar. The cloning strategy is illustrated in FIG. 11.

Several E. coli colonies (clones) could be isolated and characterized. For this purpose, the corresponding plasmid DNA was subjected to a dideoxy sequencing under conditions with which a person skilled in the art is familiar (see FIG. 12). In order to prepare the cloned DNA for the application to cell cultures and mitochondria, the cloning insert (mitochondrial transformation plasmid) was separated by the use of the restriction endonuclease Bsa I from the pBluescript vector under conditions with which a person skilled in the art is familiar. Alternatively, the insert DNA could be amplified via two oligonucleotides (primers 2 and 5; nucleotide sequence of primer 5:GATCCGGTCTCATTTTATGCG, SEQ ID NO:21) by the polymerase chain reaction. The use of S-dNTPs permitted the production of 'thionated' DNA which is stabilized over cellular nucleases. In both cases, the subsequent use of the restriction endonuclease Bsa I resulted in two different 5' overhangs. They are complementary to the 'hairpin loops' used in order to achieve a cyclization of the linear nucleic acid (see FIGS. 13a and b). The oligonucleotides are produced via chemical synthesis. As a result, they do not have phosphorylated 5' ends and have to be phosphorylated by a kinase reaction under conditions with which a person skilled in the art is familiar (in order to be able to subsequently examine the cellular transformation, [γ-$^{32}$P]-ATP was partially used in this reaction as substrate to radioactively label the plasmid). A majority of the 'hairpin loop' structure of the oligonucleotides forms spontaneously, since the palindromic sequence can hybridize with itself. However, dimers of the 'hairpin loops' can also be converted into monomers by denaturing them in the greatest possible volume (<0.1 μM) at 93° C. for at least 5 min. and fixing them immediately in a solid matrix by freezing. Then, the oligonucleotides are slowly thawed at 4° C. and then 99% thereof are available in the desired monomeric 'hairpin loop' structure (see FIG. 14).

The plasmid DNA was cyclized together with the two monomerized 'hairpin loops' (HP 1 and 2) in a reaction batch. In this case, the molar ratio of plasmid DNA to the two 'hairpin loops' was 1:100:100 (plasmid:HP1: HP2). By using the T4 DNA ligase, the individual reactants could be combined under conditions with which a person skilled in the art is familiar (see FIGS. 15a–15b). The ligation products were purified by a treatment with exonuclease III (reaction conditions: 37° C., 60 min.). While nucleic acids having free 3' ends are degraded by the nuclease, the plasmid DNA linked with the two 'hairpin loops' remains stable to the 3'-5' exonuclease activity of the enzyme. The only reaction product (see FIG. 15a) was separated via a preparative agarose gel electrophoresis and purified by an electroelution or by using QIAquick (Qiagen) in accordance with the manufacturer's recommendation.

The ligation product was examined via an RFLP analysis (restriction fragment length polymorphism). For this purpose, the ligated and purified plasmid DNA was treated with the restriction endonuclease Mae III under conditions with which a person skilled in the art is familiar. The DNA had five cleavage sites, so that fragments of differing sizes form which can be analyzed via an agarose gel (4%). FIG. 15b shows by way of example the Mae III cleavage pattern that is obtained after the ligation of the plasmid DNA with the two 'hairpin loops'. In this case, the DNA bands marked by the arrow tips represent the left and right end of the amplified (lane 1) and the linear-cyclic (lanes 2 and 3) mitochondrial plasmids.

For the conjugation of the circularized plasmid with the synthetic signal peptide of the rat ornithine transcarbamylase (H$_2$N-MLSNLRILLNKAALRKAHTSMVRNFRY GKPVQSQVQ-LKPRDLC-COOH), (SEQ ID NO:22) the nucleic acid was incubated with 20 times a molar excess of m-maleimidobenzoyl-N-hydroxysuccinimide ester (linkage agent) at 20° C. for 60 min. (incubation medium: 50 mM potassium phosphate pH 7.8). The excess linkage agent was separated by a 'nick spin column' (Pharmacia-LKB) under conditions with which a person skilled in the art is familiar. The 'activated' nucleic acid was conjugated by reacting the nucleic acid with a 50 times the molar excess of the signal peptide at 20° C. (incubation medium: 50 mM potassium phosphate pH 6.8). The reaction was stopped by the addition of 1 mM dithiothreitol after 45 min. and the conjugate was available for the experiments to come.

In order to be able to show the in vivo usability of the peptide-nucleic acid plasmid, the plasmid had to be incorporated into eukaryotic cells. For this purpose, a chloramphenicol-sensitive B lymphocyte or fibroblast cell culture was transfected via a lipotransfection with the peptide-nucleic acid plasmid: 1 μg of the radioactively labeled peptide-nucleic acid plasmid (the labeling was introduced as $^{32}$P labeling during the kinase reaction of the 'hairpin loop' (HP1)) was pre-incubated together with 2–6 μl LipofectAmine® (Gibco-BRL) in 200 μl serum-free Optimem® (Gibco-BRL) (20° C., 15 min.). During the incubation the polycationic lipid of the LipofectAmine® reagent DOSPA (2,3-dioleyloxy-N-[2-(sperminecarboxamido)-ethyl]-N,N-dimethyl-1-propaneaminiumtrifluoroacetate) forms unilamellar liposomes with the aid of the neutral lipid DOPE (dioleoylphosphatidylethanolamine), which can complex the DNA. Then, the reaction batch was added to the prepared cells, adjusted to a density of about 2.5×10$^6$ per 0.8 ml (35 mm culture dishes, 4 h, 37° C., CO$_2$ incubator). The transfection medium was then replaced by 5 ml of DMEM medium (Gibco-BRL) previously supplemented with 10% fetal calf serum and 100 μg/ml chloramphenicol. The transformation efficiency was determined by the measurement of the $^{32}$P radioactivity of the construct. As a rule, a cellular incorporation rate of 80–85% was measured. This means that 80–85% of the chimeric construct were associated with the transformed cells and 15–20% of the chimeric peptide-DNA plasmid remained in the supernatant of the transfection reaction.

After about 21–28 days, chloramphenicol-resistant colonies formed in the transformed cells. Under conditions with which a person skilled in the art is familiar, the resistant cells were isolated and multiplied. Under conditions with which a person skilled in the art is familiar, sufficient DNA could be obtained from about 1×10$^5$ cells to classify the genotypes. For this purpose, the isolated DNA was separated via agarose gel electrophoresis and transferred to a nylon membrane (Southern blot). The nucleic acids were detected by hybridization using a specific, radioactively labeled probe (see FIG. 16). In addition to the introduced circularized 'linear' vector (lanes 2 and 6) an 'in vitro' transcription (lane 3), an 'in vitro' replication (lane 4), as well as the intermediates obtained 'in vivo' (isolated nucleic acids of a transformed clone) are shown in this illustration. While the three smaller bands can be produced in vitro by incubating the circularized vector with the four nucleoside triphosphates (RNA) and a mitochondrial enzyme extract (lane 3), the formation of a dimer, circular plasmid largest band in lane 4) is observed in the further addition of the deoxynucleoside triphosphates to the reaction batch: an identical image yields the analysis of the nucleic acids which can be obtained from transformed cell colonies (lane 5). The fact that the largest DNA band in lanes 4 and 5 is actually the dimeric and thus replicated mitochondrial plasmid, could be confirmed by sequence analysis.

A lipotransfection batch where the non-conjugated plasmid not linked with the signal peptide was used, served as control experiment. As expected, this plasmid was not incorporated into the mitochondria of the transfected cells and thus did not result in the formation of chloramphenicol-resistant cells. These cells stopped growth after 10 days and decayed within the following 8 to 10 days completely.

What is claimed is:

1. A chimeric peptide-nucleic acid construct comprising:
   (a) a mitochondria-specific signal peptide, wherein the peptide does not comprise a KDEL signal sequence, and wherein the peptide has the amino acid sequence set forth in SEQ ID NO:1 or SEQ ID NO:22,
   (b) a linkage agent covalently linked to an amino acid at the carboxy-terminal end of the signal peptide, and
   (c) a linear nucleic acid, wherein said nucleic acid is covalently linked to the linkage agent,
whereby the signal peptide is linked to the nucleic acid via the linkage agent in the construct so that the chimeric peptide-nucleic acid construct enters mitochondria.

2. The chimeric peptide-nucleic acid construct of claim 1, wherein the nucleic acid has secondary structure.

3. The chimeric peptide-nucleic acid construct of claim 2, wherein the nucleic acid comprises a sequence that is capable of forming a hairpin loop structure.

4. The chimeric peptide-nucleic acid construct according to claim 1, wherein phosphodiester bonds of the nucleic acid are substituted with phosphorus thioate bonds.

5. The chimeric peptide-nucleic acid construct of claim 1, wherein the nucleic acid comprises a reactive linkage group.

6. The chimeric peptide-nucleic acid construct of claim 5, wherein the reactive linkage group contains an amino group and the linkage agent contains an amino-reactive group.

7. The chimeric peptide-nucleic acid construct of claim 5, wherein the reactive linkage group contains a thiol group and the linkage agent contains a thiol-reactive group.

8. The chimeric peptide-nucleic acid construct of claim 5, wherein the linkage group is bound to the nucleic acid via a spacer comprising at least two carbon atoms.

9. The chimeric peptide-nucleic acid construct of claim 8, wherein the linkage group present is bound to the nucleic acid via a spacer comprising six carbon atoms.

10. The chimeric peptide-nucleic acid construct of claim 6, wherein the linkage group is located at the 3' hydroxy or 3' phosphate terminus or at the 5' hydroxy or 5' phosphate terminus of the linear nucleic acid.

11. The chimeric peptide-nucleic acid construct of claim 10, wherein an additional nucleic acid, an antisense oligonucleotide, a messenger RNA or a gene which has controlled transcription and/or replication in cells is covalently linked with the 5' terminus and/or 3' terminus of the nucleic acid.

12. The chimeric peptide-nucleic acid construct of claim 11, further comprising a promoter, wherein the promoter is a mitochondrial promoter.

13. The chimeric peptide-nucleic acid construct of claim 1, wherein the signal peptide has a reactive amino acid at the carboxy-terminal end and wherein the linkage agent contains an amino-reactive or thiol-reactive group.

14. The chimeric peptide-nucleic acid construct of claim 13, wherein the reactive amino acid at the carboxyl-terminal end is lysine or cysteine.

15. The chimeric peptide-nucleic acid construct of claim 1, wherein the signal peptide comprises a mitochondria-specific peptidase cleavage site.

16. The chimeric peptide-nucleic acid construct of claim 15, wherein the peptide consists of the mitochondria-specific cleavable signal peptide of human mitochondrial ornithine transcarbamylase, extended by an cysteine at the C terminus.

17. The chimeric peptide-nucleic acid construct of claim 1, wherein the linkage agent is a bifunctional or a hetero-bifunctional cross-linker.

18. The chimeric peptide-nucleic acid construct of claim 1, wherein the linkage agent contains thiol-reactive and/or amino-reactive groups when the signal peptide and the nucleic acid carry thiol and/or amino groups as linkage sites.

19. The chimeric peptide-nucleic acid construct of claim 1, wherein the linkage agent is m-maleimido-benzoyl-N-hydroxy-succinimide ester.

20. The chimeric peptide-nucleic acid construct of claim 1, wherein the molecule penetrates mitochondrial membranes by utilizing natural transport mechanisms.

21. A method for the production of a chimeric peptide-nucleic acid construct which enters mitochondria or claim 1, said method comprising the steps of:

(a) reacting a nucleic acid or oligonucleotide containing a functional linkage group having a linkage agent to form a construct, (b) reacting of the construct of (a) with amino acids at the carboxy-terminal end of a peptide containing a signal sequence, wherein the signal sequence is not a KDEL signal sequence, and wherein the peptide has the amino acid sequence set forth in SEQ ID NO:1 or SEQ ID NO:22, to form a chimeric peptide-nucleic acid linked construct; and (c) optionally extending the chimeric peptide-nucleic acid linked construct of step (b) by binding or covalently joining a further nucleic acid molecule.

22. The method of claim 21, wherein the further nucleic acid molecule in step (c) comprises a human mitochondrial promoter of light strand ($P_L$) and a mitochondrial transfer RNA leucine ($tRNA^{LeuUUR}$) gene.

* * * * *

SEQUENCE LISTING

<160> NUMBER OF SEQ ID NOS: 22

<210> SEQ ID NO 1
<211> LENGTH: 41
<212> TYPE: PRT
<213> ORGANISM: Rattus rattus
<220> FEATURE:

<400> SEQUENCE: 1

Met Leu Ser Asn Leu Arg Ile Leu Leu Asn Lys Ala Ala Leu Arg Lys
 1               5                  10                  15

Ala His Thr Ser Met Val Arg Asn Phe Arg Tyr Gly Lys Pro Val Gln
             20                  25                  30

Ser Gln Leu Lys Pro Arg Asp Leu Cys
         35                  40

<210> SEQ ID NO 2
<211> LENGTH: 39
<212> TYPE: DNA
<213> ORGANISM: Artificial Sequence
<220> FEATURE:
<223> OTHER INFORMATION: Synthetic sequence

<400> SEQUENCE: 2
ccccgggtac cctgcgagcc ctgggctcgc aaggtaccc                      39

<210> SEQ ID NO 3
<211> LENGTH: 34
<212> TYPE: DNA
<213> ORGANISM: Homo sapiens

<400> SEQUENCE: 3
ggggccctct ctattgatga gattagtagt atgg                           34

<210> SEQ ID NO 4
<211> LENGTH: 34
<212> TYPE: DNA
<213> ORGANISM: Homo sapiens

<400> SEQUENCE: 4
ccatactact aatctcatca atagagaggg cccc                           34

<210> SEQ ID NO 5
<211> LENGTH: 30
<212> TYPE: DNA
<213> ORGANISM: Homo sapiens

<400> SEQUENCE: 5
ccatactact aatctcatca atagagaggg                                30

<210> SEQ ID NO 6
<211> LENGTH: 103
<212> TYPE: DNA
<213> ORGANISM: Artificial Sequence
<220> FEATURE:
<223> OTHER INFORMATION: Chimeric sequence

<400> SEQUENCE: 6
ccatactact aatctcatca atagagaggg ccccgggtac cttgcgagcc ctgggctcgc    60
aaggtacccg gggccctctc tattgatgag attagtagta tgg                    103

<210> SEQ ID NO 7
<211> LENGTH: 1465
<212> TYPE: DNA
<213> ORGANISM: Homo sapiens

<400> SEQUENCE: 7

```
ccgcggtggc tggcacgaaa ttgaccaacc ctggggttag tatagcttag ttaaactttc      60
gtttattgct aaaggttaat cactgctgtt tcccgtgggg gtgtggctag gctaagcgtt     120
ttgagctgca ttgctgcgtg cttgatgctt gttccttttg atcgtggtga tttagagggt     180
gaactcactg gaacgggdat gcttgcatgt gtaatcttac taagagctaa tagaaaggct     240
aggaccaaac ctatttgttt atggggtgat gtgagcccgt ctaaacattt tcagtgtatt     300
gctttgagga ggtaagctac ataaactgtg gggggtgtct ttggggtttg gttggttcgg     360
ggtatggggt tagcagcggt gtgtgtgtgc tgggtaggat gggcgggggt tgtattgatg     420
agattagtag tatgggagtg ggaggggaaa ataatgtgtt agttgggggg tgactgttaa     480
aagtgcatac cgccaaaaga taaaatttga atctggttaa ggctggtgtt agggcccttt     540
gtcccacacc cacccaagaa cagggtttgt taagatggca gagcccggta atcgcataaa     600
acttaaaact ttacagtcag aggttcaatt cctcttctta acaacatacc catggccaac     660
ctcctactcc tcattgtacc cattctaatc gcaatggcat tcctaatgct taccgaacga     720
aaaattctag gctatataca actacgcaaa ggccccaacg tggtaggccc ctacgggcta     780
ctacaacccct tcgctgacgc cataaaactc ttcaccaaag agccoctaaa acccgccaca     840
tctaccatca ccctctacat caccgccccg accttagctc tcaccatcgc tcttctacta     900
tgaaccccccc tccccatacc caaccccctg gtcaacctca acctaggcct cctatttatt     960
ctagccacct ctagcctagc cgtttactca atcctctgat cagggtgagc atcaaactca    1020
aactacgccc tgatcggcgc actgcgagca gtagcccaaa caatctcata tgaagtcacc    1080
ctagccatca ttctactatc aacattacta ataagtggcc cctttaacct ctccacccct    1140
atcacaacac aagaacacct ctgattactc ctgccatcat gacccttggc cataatatga    1200
tttatctcca cactagcaga gaccaaccga accccctttcg accttgccga agggagtcc    1260
gaactagtct caggcttcaa catcgaatac gccgcaggcc ccttcgccct attcttcata    1320
gccgaataca caaacattat tataataaac accctcacca ctacaatctt cctaggaaca    1380
acatatgacg cactctcccc tgaactctac acaacatatt ttgtcaccaa gaccctactt    1440
ctaacctccc tgttcttatg aattc                                          1465
```

<210> SEQ ID NO 8
<211> LENGTH: 1465
<212> TYPE: DNA
<213> ORGANISM: Homo sapiens

<400> SEQUENCE: 8

```
gaattcataa gaacagggag gttagaagta gggtcttggt gacaaaatat gttgtgtaga      60
gttcagggga gagtgcgtca tatgttgttc ctaggaagat tgtagtggtg agggtgttta     120
ttataataat gtttgtgtat tcggctatga agaataggge gaaggggcct gcggcgtatt     180
cgatgttgaa gcctgagact agttcggact cccttcggc aaggtcgaag ggggttcggt     240
tggtctctgc tagtgtggag ataaatcata ttatggccaa gggtcatgat ggcaggagta     300
atcagaggtg ttcttgtgtt gtgataaggg tggagaggtt aaaggagcca cttattagta     360
atgttgatag tagaatgatg gctagggtga cttcatatga gattgtttgg gctactgctc     420
```

| | |
|---|---|
| gcagtgcgcc gatcagggcg tagtttgagt ttgatgctca ccctgatcag aggattgagt | 480 |
| aaacggctag gctagaggtg gctagaataa ataggaggcc taggttgagg ttgaccaggg | 540 |
| ggttgggtat ggggaggggg gttcatagta gaagagcgat ggtgagagct aaggtcgggg | 600 |
| cggtgatgta gagggtgatg gtagatgtgg cgggttttag gggctctttg gtgaagagtt | 660 |
| ttatggcgtc agcgaagggt tgtagtagcc cgtaggggcc taccacgttg gggccttttgc | 720 |
| gtagttgtat atagcctaga attttccgtt cggtaagcat taggaatgcc attgcgatta | 780 |
| gaatgggtac aatgaggagt aggaggttgg ccatgggtat gttgttaaga agaggaattg | 840 |
| aacctctgac tgtaaagttt taagttttat gcgattaccg ggctctgcca tcttaacaaa | 900 |
| ccctgttctt gggtgggtgt gggacaaagg gccctaacac cagcctaacc agatttcaaa | 960 |
| ttttatcttt tggcggtatg cacttttaac agtcacccccc caactaacac attattttcc | 1020 |
| cctcccactc ccatactact aatctcatca atacaacccc cgcccatcct acccagcaca | 1080 |
| cacacaccgc tgctaacccc ataccccgaa ccaaccaaac cccaaagaca ccccccacag | 1140 |
| tttatgtagc ttacctcctc aaagcaatac actgaaaatg tttagacggg ctcacatcac | 1200 |
| cccataaaca aataggtttg gtcctagcct ttctattagc tcttagtaag attacacatg | 1260 |
| caagcatccc cgttccagtg agttcaccct ctaaatcacc acgatcaaaa ggaacaagca | 1320 |
| tcaagcacgc agcaatgcag ctcaaaacgc ttagcctagc cacaccccca cgggaaacag | 1380 |
| cagtgattaa cctttagcaa taaacgaaag tttaactaag ctatactaac cccagggttg | 1440 |
| gtcaatttcg tgccagccac cgcgg | 1465 |

```
<210> SEQ ID NO 9
<211> LENGTH: 86
<212> TYPE: DNA
<213> ORGANISM: Artificial Sequence
<220> FEATURE:
<223> OTHER INFORMATION: Synthetic sequence

<400> SEQUENCE: 9
```

| | |
|---|---|
| gatatcgcga agcttaaggc gcctcaggtc accatatgat catttgttaa gatggcagag | 60 |
| cccggtaatc gcataaaatg agaccg | 86 |

```
<210> SEQ ID NO 10
<211> LENGTH: 94
<212> TYPE: DNA
<213> ORGANISM: Artificial Sequence
<220> FEATURE:
<223> OTHER INFORMATION: Synthetic sequence

<400> SEQUENCE: 10
```

| | |
|---|---|
| gatccggtct cattttatgc gattaccggg ctctgccatc ttaacaaatg atcatatggt | 60 |
| gacctgaggc gccttaagct tcgcgatatc tgca | 94 |

```
<210> SEQ ID NO 11
<211> LENGTH: 1455
<212> TYPE: DNA
<213> ORGANISM: Unknown
<220> FEATURE:
<223> OTHER INFORMATION: Plasmid

<400> SEQUENCE: 11
```

| | |
|---|---|
| ctcgagggtc tcaggggcta atagaaaggc taggaccaaa cctatttgtt tatggggtga | 60 |
| tgtgagcccg tctaaacatt ttcagtgtat tgctttgagg aggtaagcta cataaactgt | 120 |
| gggggggtgtc tttggggttt ggttggttcg gggtatgggg ttagcagcgg tgtgtgtgtg | 180 |

-continued

```
ctgggtagga tgggcggggg ttgtattgat gagattagta gtatgggagt gggaggggaa      240
aataatgtgt tagttggggg gtgactgtta aaagtgcata ccgccaaaag ataaaatttg      300
aaatctggtt aggctggtgt tagggttctt tgttttttggg gtttggcaga gatgtgttta    360
agtgctgtgg ccagaagcgg gggagggggg gtttggtgga aatttttttgt tatgatgtct   420 gtgtggaaag tggctgtgca gacattcaat tgttattatt atgtcctaca agcattaatt    480
aattaacaca ctttagtaag tatgttcgcc tgtaatattg aacgtaggtg cgataaataa     540
taggatgagg caggaatcaa agacagatac tgcgacatag ggtgctccgg ctccagcgtc    600
tcgcaatgct atcgcgtgca tacccccag acgaaaatac caaatgcatg gagagctccc      660
gtgagtggtt ataggggtga tagacctgtg atccatcgtg atgtcttatt taaggggaac    720
gtgtgggcta tttaggcttt atgaccctga agtaggaacc agatgtcgga tacagttcac    780
tttagctacc cccaagtgtt atgggcccgg agcgaggaga gtagcactct tgtgcgggat    840
attgatttca cggaggatgg tggtcaaggg acccctatct gaggggggtc atccatgggg    900
acgagaaggg atttgactgt aatgtgctat gtacggtaaa tggctttatg tactatgtac     960
tgttaagggt gggtaggttt gttggtatcc tagtgggtga ggggtggctt tggagttgca   1020
gttgatgtgt gatagttgag ggttgattgc tgtacttgct tgtaagcatg gggagggggt   1080
tttgatgtgg attgggtttt tatgtactac aggtggtcaa gtatttatgg taccgtacaa    1140
tattcatggt ggctggcagt aatgtacgaa atacatagcg gttgttgatg ggtgagtcaa   1200
tacttgggtg gtacccaaat ctgcttcccc atgaaagaac agagaatagt ttaaattaga   1260
atcttagctt tgggtgctaa tggtggagtt aaagactttt tctctgattt gtccttggaa    1320
aaaggttttc atctccggtt tacaagactg gtgtattagc tgcagatatc gcgaagctta   1380
aggcgcctca ggtcaccata tgatcatttg ttaagatggc agagcccggt aatcgcataa   1440
aatgagaccg gatcc                                                      1455
```

<210> SEQ ID NO 12
<211> LENGTH: 1455
<212> TYPE: DNA
<213> ORGANISM: Unknown
<220> FEATURE:
<223> OTHER INFORMATION: Plasmid

<400> SEQUENCE: 12

```
ggatccggtc tcattttatg cgattaccgg gctctgccat cttaacaaat gatcatatgg     60
tgacctgagg cgccttaagc ttcgcgatat ctgcagctaa tacaccagtc ttgtaaaccg    120
gagatgaaaa cctttttcca aggacaaatc agagaaaaag tctttaactc caccattagc    180
acccaaagct aagattctaa tttaaactat tctctgttct ttcatgggga agcagatttg     240
ggtaccaccc aagtattgac tcacccatca acaaccgcta tgtatttcgt acattactgc     300
cagccaccat gaatattgta cggtaccata aatacttgac cacctgtagt acataaaaac    360
ccaatccaca tcaaaacccc ctccccatgc ttacaagcaa gtacagcaat caaccctcaa    420
ctatcacaca tcaactgcaa ctccaaagcc acccctcacc cactaggata ccaacaaacc    480
tacccaccct taacagtaca tagtacataa agccatttac cgtacatagc acattacagt    540
caaatccctt ctcgtcccca tggatgaccc ccctcagata ggggtccctt gaccaccatc    600
ctccgtgaaa tcaatatccc gcacaagagt gctactctcc tcgctccggg cccataacac    660
ttgggggtag ctaaagtgaa ctgtatccga catctggttc ctacttcagg gtcataaagc     720
```

```
ctaaatagcc cacacgttcc ccttaaataa gacatcacga tggatcacag gtctatcacc    780
ctattaacca ctcacgggag ctctccatgc atttggtatt ttcgtctggg gggtatgcac    840
gcgatagcat tgcgagacgc tggagccgga gcaccctatg tcgcagtatc tgtctttgat    900
tcctgcctca tcctattatt tatcgcacct acgttcaata ttacaggcga acatacttac    960
taaagtgtgt taattaatta atgcttgtag gacataataa taacaattga atgtctgcac   1020
agccactttc cacacagaca tcataacaaa aaatttccac caaaccccc ctccccgct    1080 tctggccaca gcacttaaac acatctctgc caaaccccaa aaacaaagaa ccctaacacc   1140
agcctaacca gatttcaaat tttatctttt ggcggtatgc acttttaaca gtcacccccc   1200
aactaacaca ttattttccc ctcccactcc catactacta atctcatcaa tacaaccccc   1260
gcccatccta cccagcacac acacaccgct gctaaccccta taccccgaac caaccaaacc   1320
ccaaagacac cccccacagt ttatgtagct tacctcctca aagcaataca ctgaaaatgt   1380
ttagacgggc tcacatcacc ccataaacaa ataggtttgg tcctagcctt tctattagcc   1440
cctgagaccc tcgag                                                    1455

<210> SEQ ID NO 13
<211> LENGTH: 3232
<212> TYPE: DNA
<213> ORGANISM: Unknown
<220> FEATURE:
<223> OTHER INFORMATION: Plasmid

<400> SEQUENCE: 13
ctcgagggtc tcaggggcta atagaaaggc taggaccaaa cctatttgtt tatggggtga     60
tgtgagcccg tctaaacatt ttcagtgtat tgctttgagg aggtaagcta cataaactgt    120 gggggtgtc tttggggttt ggttggttcg gggtatgggg ttagcagcgg tgtgtgtgtg    180
ctgggtagga tgggcggggg ttgtattgat gagattagta gtatgggagt gggaggggaa    240
aataatgtgt tagttggggg gtgactgtta aaagtgcata ccgccaaaag ataaaatttg    300
aaatctggtt aggctggtgt tagggttctt tgttttttggg gtttggcaga gatgtgttta    360
agtgctgtgg ccagaagcgg gggaggggg gtttggtgga aattttttgt tatgatgtct    420
gtgtggaaag tggctgtgca gacattcaat tgttattatt atgtcctaca agcattaatt    480
aattaacaca ctttagtaag tatgttcgcc tgtaatattg aacgtaggtg cgataaataa    540
taggatgagg caggaatcaa agacagatac tgcgacatag ggtgctccgg ctccagcgtc    600
tcgcaatgct atcgcgtgca taccccccag acgaaaatac caaatgcatg gagagctccc    660
gtgagtggtt aataggggtga tagacctgtg atccatcgtg atgtcttatt aagggggaac    720
gtgtgggcta tttaggcttt atgaccctga gtaggaacc agatgtcgga tacagttcac    780
tttagctacc cccaagtgtt atgggcccgg agcgaggaga gtagcactct tgtgcgggat    840
attgatttca cggaggatgg tggtcaaggg acccctatct gagggggggtc atccatgggg    900 acgagaaggg atttgactgt aatgtgctat gtacggtaaa tggctttatg tactatgtac    960
tgttaagggt gggtaggttt gttggtatcc tagtgggtga gggtggctt tggagttgca   1020 gttgatgtgt gatagttgag ggttgattgc tgtacttgct tgtaagcatg gggaggggt   1080 tttgatgtgg attgggtttt tatgtactac aggtggtcaa gtatttatgg taccgtacaa   1140
tattcatggt ggctggcagt aatgtacgaa atacatagcg gttgttgatg ggtgagtcaa   1200
tacttgggtg gtacccaaat ctgcttcccc atgaaagaac agagaatagt ttaaattaga   1260
atcttagctt tgggtgctaa tggtggagtt aaagactttt tctctgattt gtccttggaa   1320
```

-continued

```
aaaggttttc atctccggtt tacaagactg gtgtattagc tgcagatatc gcgaagcttg    1380
taacatggta agtgtactgg aaagtgcact tggacgaacc agagtgtagc ttaacacaaa    1440
gcacccaact tacacttagg agatttcaac ttaacttgac cgctctgagc taaacctagc    1500
cccaaaccca ctccacctta ctaccagaca accttagcca aaccatttac ccaaataaag    1560
tataggcgat agaaattgaa acctggcgca atagatatag taccgcaagg gaaagatgaa    1620
aaattataac caagcataat atagcaagga ctaaccccta taccttctgc ataatgaatt    1680
aactagaaat aactttgcaa ggagagccaa agctaagacc cccgaaacca gacgagctac    1740
ctaagaacag ctaaaagagc acacccgtct atgtagcaaa atagtgggaa gatttatagg    1800
tagaggcgac aaacctaccg agcctggtga tagctggttg tccaagatag aatcttagtt    1860
caactttaaa tttgcccaca gaaccctcta aatccccttg taaatttaac tgttagtcca    1920
aagaggaaca gctctttgga cactaggaaa aaaccttgta gagagagtaa aaaatttaac    1980
acccatagta ggcctaaaag cagccaccaa ttaagaaagc gttcaagctc aacacccact    2040
acctaaaaaa tcccaaacat ataactgaac tcctcacacc caattggacc aatctatcac    2100
cctatagaag aactaatgtt agtataagta acatgaaaac attctcctcc gcataagcct    2160
gcgtcagatt aaaacactga actgacaatt aacagcccaa tatctacaat caaccaacaa    2220
gtcattatta ccctcactgt caacccaaca caggcatgct cataaggaaa ggttaaaaaa    2280
agtaaaagga actcggcaaa tcttaccccg cctgtttacc aaaaacatca cctctagcat    2340
caccagtatt agaggcaccg cctgcccagt gacacatgtt taacggccgc ggtaccctaa    2400
ccgtgcaaag gtagcataat cacttgttcc ttaaataggg acctgtatga atggctccac    2460
gagggttcag ctgtctctta cttttaacca gtgaaattga cctgcccgtg aagaggcggg    2520
cataacacag caagacgaga agacccctatg gagctttaat ttattaatgc aaacagtacc    2580
taacaaaccc acaggtccta aactaccaaa cctgcattaa aaatttcggt tggggcgacc    2640
tcggagcaga acccaaccte cgagcagtac atgctaagac ttcaccagtc aaagcgaact    2700
actatactca attgatccaa taacttgacc aacggaacaa gttaccctag ggataacagc    2760
gcaatcctat tctagagtcc atatcaacaa tagggtttac gacctcgatg ttggatcagg    2820
acatcccgat ggtgcagccg ctattaaagg ttcgtttgtt caacgattaa agtcctacgt    2880
gatctgagtt cagaccggag taatccaggt cggtttctat ctaccttcaa attcctccct    2940
gtacgaaagg acaagagaaa taaggcctac ttcacaaagc gccttccccc gtaaatgata    3000
tcatctcaac ttagtattat acccacaccc acccaagaac agggtttgtt aagatggcag    3060
agcccggtaa tcgcataaaa cttaaaaactt tacagtcaga ggttcaattc ctcttcttaa    3120
caacataccc atggccaacc tcctactcct cattgtaccc attctaatcg caatggctga    3180
tcatttgtta agatggcaga gcccggtaat cgcataaaat gagaccggat cc             3232
```

<210> SEQ ID NO 14
<211> LENGTH: 3232
<212> TYPE: DNA
<213> ORGANISM: Unknown
<220> FEATURE:
<223> OTHER INFORMATION: Plasmid

<400> SEQUENCE: 14

```
ggatccggtc tcattttatg cgattaccgg gctctgccat cttaacaaat gatcagccat      60
tgcgattaga atgggtacaa tgaggagtag gaggttggcc atgggtatgt tgttaagaag     120
```

-continued

| | | |
|---|---|---|
| aggaattgaa cctctgactg taaagttta agtttatgc gattaccggg ctctgccatc | 180 |
| ttaacaaacc ctgttcttgg gtgggtgtgg gtataatact aagttgagat gatatcattt | 240 |
| acggggaag gcgctttgtg aagtaggcct tatttctctt gtcctttcgt acagggagga | 300 |
| atttgaaggt agatagaaac cgacctggat tactccggtc tgaactcaga tcacgtagga | 360 |
| ctttaatcgt tgaacaaacg aacctttaat agcggctgca ccatcgggat gtcctgatcc | 420 |
| aacatcgagg tcgtaaaccc tattgttgat atggactcta gaataggatt gcgctgttat | 480 |
| ccctagggta acttgttccg ttggtcaagt tattggatca attgagtata gtagttcgct | 540 |
| ttgactggtg aagtcttagc atgtactgct cggaggttgg gttctgctcc gaggtcgccc | 600 |
| caaccgaaat ttttaatgca ggtttggtag tttaggacct gtgggtttgt taggtactgt | 660 |
| ttgcattaat aaattaaagc tccataggggt cttctcgtct tgctgtgtta tgcccgcctc | 720 |
| ttcacgggca ggtcaatttc actggttaaa agtaagagac agctgaaccc tcgtggagcc | 780 |
| attcatacag gtccctattt aaggaacaag tgattatgct acctttgcac ggttagggta | 840 |
| ccgcggccgt taaacatgtg tcactgggca ggcggtgcct ctaatactgg tgatgctaga | 900 |
| ggtgatgttt ttggtaaaca ggcggggtaa gatttgccga gttccttta cttttttaa | 960 |
| cctttcctta tgagcatgcc tgtgttgggt tgacagtgag ggtaataatg acttgttggt | 1020 |
| tgattgtaga tattgggctg ttaattgtca gttcagtgtt ttaatctgac gcaggcttat | 1080 |
| gcggaggaga atgttttcat gttacttata ctaacattag ttcttctata gggtgataga | 1140 |
| ttggtccaat tgggtgtgag gagttcagtt atatgtttgg gattttttag gtagtgggtg | 1200 |
| ttgagcttga acgctttctt aattggtggc tgcttttagg cctactatgg gtgttaaatt | 1260 |
| ttttactctc tctacaaggt ttttcctag tgtccaaaga gctgttcctc tttggactaa | 1320 |
| cagttaaatt tacaagggga tttagagggt tctgtgggca aatttaaagt tgaactaaga | 1380 |
| ttctatcttg gacaaccagc tatcaccagg ctcggtaggt ttgtcgcctc tacctataaa | 1440 |
| tcttcccact attttgctac atagacgggt gtgctctttt agctgttctt aggtagctcg | 1500 |
| tctggtttcg ggggtcttag ctttggctct ccttgcaaag ttatttctag ttaattcatt | 1560 |
| atgcagaagg tataggggtt agtccttgct atattatgct tggttataat ttttcatctt | 1620 |
| tcccttgcgg tactatatct attgcgccag gtttcaattt ctatcgccta actttattt | 1680 |
| gggtaaatgg tttggctaag gttgtctggt agtaaggtgg agtgggtttg gggctaggtt | 1740 |
| tagctcagag cggtcaagtt aagttgaaat ctcctaagtg taagttgggt gctttgtgtt | 1800 |
| aagctacact ctggttcgtc caagtgcact ttccagtaca cttaccatgt tacaagcttc | 1860 |
| gcgatatctg cagctaatac accagtcttg taaaccggag atgaaaacct ttttccaagg | 1920 |
| acaaatcaga gaaaagtct ttaactccac cattagcacc caaagctaag attctaattt | 1980 |
| aaactattct ctgttctttc atggggaagc agatttgggt accacccaag tattgactca | 2040 |
| cccatcaaca accgctatgt atttcgtaca ttactgccag ccaccatgaa tattgtacgg | 2100 |
| taccataaat acttgaccac ctgtagtaca taaaaaccca atccacatca aaacccctc | 2160 |
| cccatgctta caagcaagta cagcaatcaa ccctcaacta tcacacatca actgcaactc | 2220 |
| caaagccacc cctcacccac taggatacca acaaacctac ccacccttaa cagtacatag | 2280 |
| tacataaagc catttaccgt acatagcaca ttacagtcaa atcccttctc gtccccatgg | 2340 |
| atgacccccc tcagatagggg gtcccttgac caccatcctc cgtgaaatca atatcccgca | 2400 |
| caagagtgct actctcctcg ctccgggccc ataacacttg ggggtagcta aagtgaactg | 2460 |
| tatccgacat ctggttccta cttcagggtc ataaagccta aatagcccac acgttcccct | 2520 |

```
taaataagac atcacgatgg atcacaggtc tatcaccca ttaaccactc acgggagctc    2580
tccatgcatt tggtattttc gtctgggggg tatgcacgcg atagcattgc gagacgctgg    2640
agccggagca ccctatgtcg cagtatctgt ctttgattcc tgcctcatcc tattatttat    2700
cgcacctacg ttcaatatta caggcgaaca tacttactaa agtgtgttaa ttaattaatg    2760
cttgtaggac ataataataa caattgaatg tctgcacagc cactttccac acagacatca    2820
taacaaaaaa tttccaccaa accccccctc ccccgcttct ggccacagca cttaaacaca    2880
tctctgccaa accccaaaaa caagaaccc taaccagc ctaaccagat ttcaaatttt    2940
atcttttggc ggtatgcact tttaacagtc accccccaac taacacatta ttttcccctc    3000
ccactcccat actactaatc tcatcaatac aaccccgcc catcctaccc agcacacaca    3060
caccgctgct aaccccatac cccgaaccaa ccaaacccca aagacacccc ccacagttta    3120
tgtagcttac ctcctcaaag caatacactg aaaatgttta gacgggctca catcaccccca    3180 taaacaaata ggtttggtcc tagcctttct attagcccct gagaccctcg ag            3232
```

<210> SEQ ID NO 15
<211> LENGTH: 39
<212> TYPE: DNA
<213> ORGANISM: Artificial Sequence
<220> FEATURE:
<223> OTHER INFORMATION: Synthetic sequence

<400> SEQUENCE: 15

```
ttttgcagct ggatcccggg cagcccggga tccagctgc                            39
```

<210> SEQ ID NO 16
<211> LENGTH: 4
<212> TYPE: PRT
<213> ORGANISM: Artificial Sequence
<220> FEATURE:
<223> OTHER INFORMATION: Synthetic sequence

<400> SEQUENCE: 16

Lys Asp Glu Leu
 1

<210> SEQ ID NO 17
<211> LENGTH: 11
<212> TYPE: DNA
<213> ORGANISM: Artificial Sequence
<220> FEATURE:
<223> OTHER INFORMATION: Primer

<400> SEQUENCE: 17

```
tgtagctgca g                                                          11
```

<210> SEQ ID NO 18
<211> LENGTH: 23
<212> TYPE: DNA
<213> ORGANISM: Artificial Sequence
<220> FEATURE:
<223> OTHER INFORMATION: Primer

<400> SEQUENCE: 18

```
ttgcatgctc gagggtctca ggg                                             23
```

<210> SEQ ID NO 19
<211> LENGTH: 11
<212> TYPE: DNA
<213> ORGANISM: Artificial Sequence -continued

```
<220> FEATURE:
<223> OTHER INFORMATION: Primer

<400> SEQUENCE: 19
cctctaagct t                                                          11

<210> SEQ ID NO 20
<211> LENGTH: 11
<212> TYPE: DNA
<213> ORGANISM: Artificial Sequence
<220> FEATURE:
<223> OTHER INFORMATION: Primer

<400> SEQUENCE: 20
gcattactag t                                                          11

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21
gatccggtct cattttatgc g                                               21

<210> SEQ ID NO 22
<211> LENGTH: 43
<212> TYPE: PRT
<213> ORGANISM: Rattus rattus

<400> SEQUENCE: 22

Met Leu Ser Asn Leu Arg Ile Leu Leu Asn Lys Ala Ala Leu Arg Lys
 1               5                  10                  15

Ala His Thr Ser Met Val Arg Asn Phe Arg Tyr Gly Lys Pro Val Gln
                20                  25                  30

Ser Gln Val Gln Leu Lys Pro Arg Asp Leu Cys
            35                  40
```